US006713247B1

(12) United States Patent
Sah et al.

(10) Patent No.: US 6,713,247 B1
(45) Date of Patent: *Mar. 30, 2004

(54) HUMAN CNS CELL LINES AND METHODS OF USE THEREFOR

(75) Inventors: Dinah W. Y. Sah, San Diego, CA (US); Fred H. Gage, La Jolla, CA (US); Jasodhara Ray, San Diego, CA (US)

(73) Assignee: Signal Pharmaceuticials, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/711,628

(22) Filed: Sep. 3, 1996

(51) Int. Cl.⁷ .............................. C12N 5/08; C12N 5/00; C12N 15/63; C12Q 1/00
(52) U.S. Cl. ..................... 435/4; 435/69.1; 435/325; 435/366; 435/368; 435/455; 435/456
(58) Field of Search ........................ 435/325, 320.1, 435/4, 69.1, 455, 456; 424/93.21

(56) References Cited

U.S. PATENT DOCUMENTS

| | | | |
|---|---|---|---|
| 5,082,670 A | | 1/1992 | Gage et al. ............ 424/520 |
| 5,196,315 A | | 3/1993 | Ronnett et al. ............ 435/29 |
| 5,270,191 A | * | 12/1993 | McKay et al. ............ 435/172.3 |
| 5,411,883 A | | 5/1995 | Boss et al. ............ 435/29 |
| 5,654,183 A | | 8/1997 | Anderson et al. ............ 435/456 |
| 5,693,511 A | * | 12/1997 | Harris et al. ............ 435/172.3 |
| 5,750,376 A | | 5/1998 | Weiss et al. ............ 435/69.52 |
| 5,849,553 A | | 12/1998 | Anderson et al. ............ 435/467 |
| 5,928,947 A | | 7/1999 | Anderson et al. ............ 435/455 |
| 6,197,585 B1 | | 3/2001 | Stringer ............ 435/368 |
| 2001/0033835 A1 | * | 10/2001 | Daley et al. ............ 424/93.21 |

FOREIGN PATENT DOCUMENTS

| | | |
|---|---|---|
| GB | 2 294 946 A | 5/1996 |
| WO | WO 89/09816 | 10/1989 |
| WO | WO 93/01275 | 1/1993 |
| WO | WO 94/09118 | 4/1994 |
| WO | WO 94/09119 | 4/1994 |
| WO | WO 94/10292 | 5/1994 |
| WO | WO 94/16059 | 7/1994 |
| WO | WO 94/16718 | 8/1994 |
| WO | WO 96/14400 | 5/1996 |

OTHER PUBLICATIONS

JD Watson et al., Recombinant DNA, "The Genes behind the Functioning of the Brain," 1997, 2nd Ed., pp. 413–417.*

Hoshimaru et al., Proceedings of the National Academy of Sciences, USA, vol. 93, pp. 1518–1523, Feb. 1996.*

Galiana et al., Journal of Neuroscience Research, vol. 36, pp. 133–146, Oct. 1, 1993.*

Rinehart et al., Carcinogenesis, vol. 14, pp. 993–999, May 1993.*

Buc–Caron, "Neuroepithelial progenitor cells explanted from human fetal brain proliferate and differentiate in vitro," *Neurobiology of Disease* 2:37–47, 1995.

Cattaneo and McKay, "Proliferation and differentiation of neuronal stem cells regulated by nerve growth factor," *Nature* 347:762–765, 1990.

Maisonpierre et al., "Neutrophin–3: A Neurotrophic Factor related to NGF and BDNF," *Science* 247:1446–1451, 1990.

Martínez–Serrano and Björklund, "Immortalized neural progenitor cells for CNS gene transfer and repair," *Trends Neurosci.* 20(11):530–538, 1997.

Sah et al., "Bipotent progenitor cell lines from the human CNS," *Nature Biotechnology* 15(6): 574–580, 1997.

Sah et al., "Conditional Immortalization of Human Neuronal, Glial and Multi–Potent CNS Progenitor Cells," *Society For Neuroscience Abstracts* 22(1–3): p. 29, Abstract No. 21.12, 1996.

Saneto and de Vellis, *Neurochemistry: A Practical Approach*, IRL Press, Washington, DC, 1987, Chapter 2, "Neuronal and glial cells: cell culture of the central nervous system," pp. 27–63.

Walicke et al., "Fibroblast growth factor promotes survival of dissociated hippocampal neurons and enhances neurite extension," *Proc. Natl. Acad. Sci. USA* 83: 3012–3016, 1986.

Gallyas et al., "Identifying Monoaminergic, GABAergic, and Cholinergic Characteristics in Immortalized Neuronal Cell Lines," Neurochemical Res. 22(5):569–575 (1997).

Hoshimaru et al., "Differentiation of the Immortalized Adult Neuronal Progenitor Cell Line HC2S2 into Neurons by Regulatable Suppression of the v–*myc* Oncogene," Proc. Natl. Acad. Sci. USA 93:1518–1523 (1996).

Prasad et al., "Establishment and Characterization of Immortalized Clonal Cell Lines from Fetal Rat Mesencephalic Tissue," In Vitro Cell. Devel. Biol. 30A:596–603 (1994).

* cited by examiner

*Primary Examiner*—Anne-Marie Falk
(74) *Attorney, Agent, or Firm*—Pennie & Edmonds LLP

(57) ABSTRACT

Conditionally-immortalized human CNS progenitor cell lines are provided. Such cell lines, which may be clonal, may be used to generate neurons and/or astrocytes. Such cell lines and/or differentiated cells may be used for the development of therapeutic agents to prevent and treat a variety of CNS-related diseases. Such cell lines and/or differentiated cells may also be used in assays and for the general study of CNS cell development, death and abnormalities.

23 Claims, 27 Drawing Sheets

MAP2a/b

GFAP

HUMAN CNS CELL LINES AND METHODS OF USE THEREFOR

TECHNICAL FIELD

The present invention relates generally to CNS cell lines. The invention is more particularly related to conditionally-immortalized human CNS progenitor cell lines and to differentiated cells derived from such cell lines. Such cell lines and/or differentiated cells may be used in the development of therapeutic agents for the prevention and treatment of neurological diseases and other conditions. The present invention is also related to the use of such cell lines and/or differentiated cells in assays and for the study of CNS cell development, death and abnormalities.

BACKGROUND OF THE INVENTION

The development of therapies for central nervous system (CNS) disorders has been hampered by the lack of human cells for research and development. Human CNS tissue is difficult to obtain and is not available on a regular basis. Primary human CNS cultures derived from such tissue generally express neuronal markers and contain functional ion channels and neurotransmitter receptors, but such cultures have a limited life span (about one month), necessitating frequent dissections and plating. Accordingly, neither tissue nor primary cultures are capable of supplying the cells needed for extensive research and development.

Drug development is generally carried out using immortalized rodent cells, and the results are then extrapolated to humans. Rodent neuronal progenitor cells have been immortalized with, for example, retroviral vectors encoding the myc oncogene or SV40 large T antigen (Bartlett et al., *Proc. Natl. Acad. Sci. USA* 85:3255–3259, 1988); Cepko, *Ann. Rev. Neurosci.* 12:47–65, 1989; Eves et al., *Proc. Natl. Acad. Sci. USA* 89:4373–4377, 1992; Frederiksen et al., *Neuron* 1:439–448, 1988; Gage et al., *Ann. Rev. Neurosci.* 18:159–192, 1995; Gao and Hatten, *Development* 120:1059–1070, 1994; Giordano et al., *Exp. Neurol.* 124:395–400, 1993; Lendhal and McKay, *TINS* 13:132–137, 1990; Mehler et al., *Nature* 362:62–65, 1993; Renfranz et al., *Cell* 66:713–729, 1988; Ryder et al., *J. Neurobio.* 21:356–375, 1990; White et al., *J. Neurosci.* 14:6744–6753, 1994; Whittemore and White, *Brain Res.* 615:27–40, 1993). However, in v-myc immortalized cells, the mitotic activity of the oncogene is always present; cells do not undergo differentiation, and channels and receptors are not functional. To allow differentiation, a temperature-sensitive mutant of SV40 large T-antigen (tsA58) has been used (Eves et al., *Proc. Natl. Acad. Sci. USA* 89:4373–4377, 1992; Mehler et al., *Nature* 362:62–65, 1993). At the nonpermissive temperature (39° C.) the expression of T-antigen in transfected cells is considerably down-regulated. However, the progenitor cells can undergo only incomplete differentiation into neurons (Frederiksen et al., *Neuron* 1:439–448, 1988; Gao and Hatten; *Development* 120:1059–1070, 1994; Mehler et al., *Nature* 362:62–65, 1993; Renfranz et al., *Cell* 66:713–729, 1988; White et al., *J. Neurosci.* 14:6744–6753, 1994; Whittemore and White, *Brain Res.* 615:27–40, 1993). A combination of factors and substrates is needed to differentiate the cells further in vitro, and complete differentiation of these cells has not been achieved. In addition, species differences continue to render the use of rat CNS cells problematic. In particular, the small variations in specific protein sequences between species may translate into significant effects when pharmacological agonists or antagonists are examined.

Cloned human CNS channels and receptors provide a potential solution to this problem, but such cloned proteins are not present in their native environment (typically they are expressed in cell lines derived from non-CNS tissue, such as kidney (HEK 293) or cervical (HeLa) cells) and downstream signaling pathways are abnormal. Moreover, these receptors are heteromultimeric proteins and, while the exact stoichiometry of subunits is not known, it is likely that there are numerous subtypes with different subunit compositions. Expressed receptor subunit combinations are artificial and may not reflect those in vivo, and attempts to match native receptors with heterologously expressed subunits have not been successful in a number of cases. Consequently, expressed channels and receptors differ fundamentally from their native counterparts and are not optimal for drug development.

Human CNS lines containing functional native channels and receptors in their normal cellular environment would provide an infinite and homogeneous source of human CNS cells and would offer significant advantages for CNS drug discovery. Currently, the only human cell line that can be differentiated into postmitotic CNS neurons is a human teratocarcinoma cell line (NT2) that requires 6–10 weeks of complex in vitro manipulations for neuronal differentiation (Younkin et al., *Proc. Natl. Acad. Sci. USA* 90:2174–2178, 1993). This lengthy time period is inconvenient for basic research and prohibitive for use in high-throughput screens of thousands of compounds. Human CNS lines that can be differentiated in a shorter period of time into neurons expressing functional receptors would clearly be preferable. Thus far, however, it has not been possible to generate such cell lines, and the techniques for generating the rat progenitor cell lines have been largely unsuccessful when applied to human cells.

Accordingly, there is a need in the art for human CNS lines that may be readily differentiated and that express channels and receptors in their native forms. The present invention fulfills these needs and further provides other related advantages.

SUMMARY OF THE INVENTION

Briefly stated, the present invention provides conditionally-immortalized human CNS progenitor cell lines capable of differentiation into astrocytes and/or neurons. In one aspect, the present invention provides a method for producing a conditionally-immortalized human CNS progenitor cell, comprising (a) plating human progenitor cells on a surface that permits proliferation; (b) adding growth medium to the cells; (c) transfecting the cells with DNA encoding a selectable marker and regulatable growth-promoting gene under conditions promoting expression of the growth-promoting gene; (d) passaging the transfected cells onto a substrate; and (e) adding growth medium supplemented with one or more proliferation-enhancing factors to the transfected cells.

In a related aspect, the present invention provides a conditionally-immortalized clonal human CNS progenitor cell capable of differentiation into neurons and astrocytes.

In another aspect, a method for producing astrocytes and/or neurons is provided comprising culturing a cell produced as described above under conditions inhibiting expression of the growth-promoting gene. In a related aspect, astrocytes and neurons prepared as described above are provided.

In yet another aspect, the present invention provides a method for introducing a CNS cell into a mammal, comprising administering to a mammal a cell as described above.

In a related aspect, a method for treating a patient is provided, comprising administering to a patient a cell as described above.

In a further aspect, the present invention provides methods for screening for an agent that modulates activity of a protein produced by a CNS cell, comprising (a) contacting a cell as described above and (b) subsequently measuring the ability of said candidate agent to modulate activity of a protein produced by said cell.

In yet another aspect, a method for detecting the presence or absence of a protein in a sample is provided comprising (a) contacting a sample with a cell as described above and (b) subsequently detecting a response in said cell, and thereby detecting the presence of a protein in said sample.

In a further aspect, the present invention provides a method for identifying a human CNS gene or protein, comprising detecting the presence of a gene or protein within a culture of cells as described above.

In another aspect, a method is provided for screening for an agent that affects CNS cell death, comprising (a) contacting a cell as described above with a candidate agent under conditions that, in the absence of candidate agent, result in death of said cell and (b) subsequently measuring the ability of said candidate agent to affect the death of said cell.

In a related aspect, the present invention provides a method for screening for a protein that regulates CNS cell death, comprising (a) altering the level of expression of a protein within a cell as described above and (b) subsequently measuring the affect of said alteration on the death of said cell, and thereby identifying a protein that regulates CNS cell death.

In a further aspect, conditionally-immortalized human CNS progenitor cells are provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 6A shows the sodium current, FIG. 6B shows the NMDA current, FIG. 6C shows the kainate current and FIG. 6D shows the GABA current. In each case, the current without differentiation (column 1, FGF-2) is shown, along with the current in cells differentiated with tetracycline (Tc) alone (column 2); Tc, high $K^+$, NT-3 and BDNF (column 3); Tc and RA (column 4); Tc and FSK (column 5) and Tc and dbcAMP (column 6).

In FIGS. 25B and 25C, the immunoreactivity was also evaluated in cells grown intetracycline and RA for one week (Tc/RA, columns 5–6) and in cells grown in tetracycline, high $K^+$, NT-3 and BDNF for one week (Tc/K/N/B, columns 7–8).

(FIG. 26C, hatched bars). In each case, the immunoreactivity was evaluated in cells grown in proliferative conditions (growth medium containing FGF-2, EGF, PDGF and conditioned medium, columns 1–2); in the presence of tetracycline for one week (Tc, columns 3–4); in tetracycline and RA for one week (Tc/RA, columns 5–6) and in cells grown in tetracycline, high K+, NT-3 and BDNF for one week (Tc/K/N/B, columns 7–8).

DETAILED DESCRIPTION OF THE INVENTION

Figure 1:
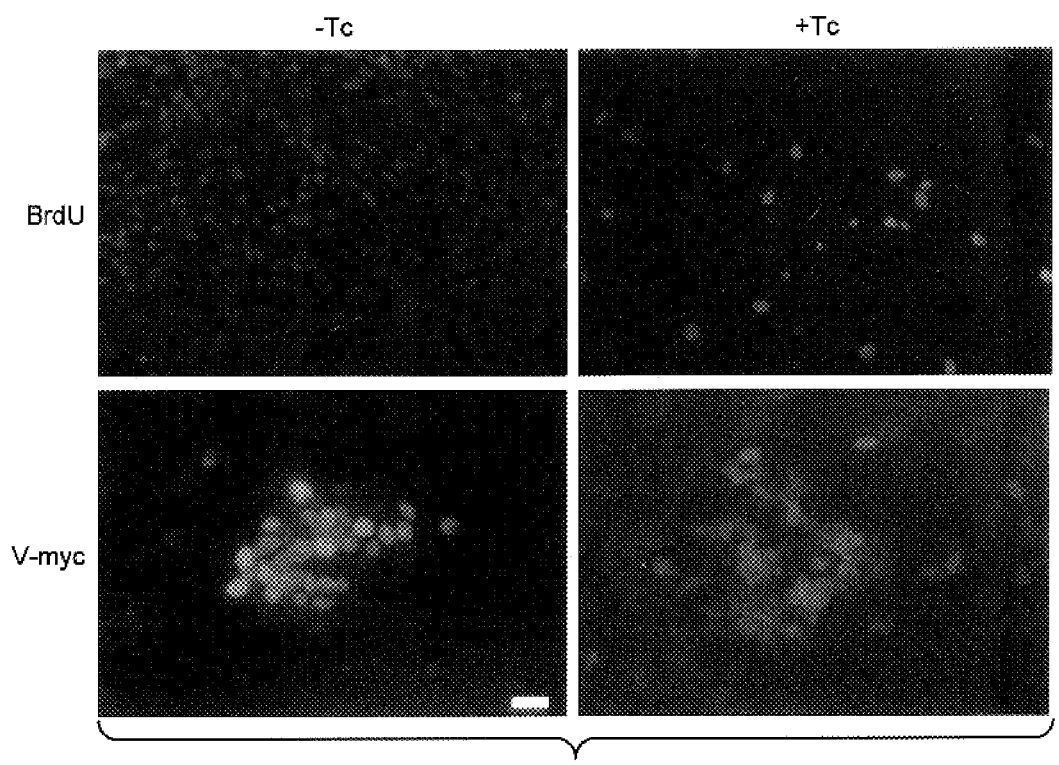
FIG. 1 is a photograph of representative immortalized human CNS progenitor cells stained for BrdU or v-myc, after growth in the absence (−) or presence (+) of tetracycline (Tc, 1 µg/mL for 6 days). The calibration bar represents 20 µM.

As noted above, the, present invention is generally directed to conditionally-immortalized human CNS progenitor cell lines, differentiated cells generated from such cell lines and methods of using such progenitor and/or differentiated cells. In particular, the present invention is directed to conditionally-immortalized human CNS progenitor cell lines capable of differentiation (within a relatively short period of time) into astrocytes and/or neurons, and to the use of such compositions for drug discovery and development, transplantation studies, therapeutic methods and a variety of assays. Conditionally-immortalized human CNS progenitor cell lines of the present invention may, but need not, be clonal cell lines. The cell lines described herein provide an infinite, renewable supply of homogeneous cells and further facilitate CNS drug development by circumventing the problems associated with species differences, the lack of a.native cellular environment and variations in endogenous subunit combinations. Furthermore, since the immortalization process arrests cells at specific stages of development, cells at particular stages in the lineage can be isolated, characterized and used in a variety of methods described herein. Such cell lines can differentiate into cells expressing specific receptor subtype profiles and can provide information about the existence of multi-potent, neuronal and glial progenitor cells in the human CNS.

Conditionally-immortalized human progenitor cells may generally be prepared from any human fetal or adult tissue that contains progenitor cells. Suitable tissues will be apparent to one of ordinary skill in the art, and include unspecified or specified regions such as, but not limited to, hippocampus, septal nuclei, cortex, cerebellum, ventral mesencephalon and/or spinal cord. Preferably, the tissue source is human fetal CNS tissue which may be obtained from, for example, Advanced Bioscience Resources, Inc. (Alameda, Calif.). Fragments of the tissue are first dissociated using standard techniques to yield a single-cell suspension. The cells are then plated on a surface that does not substantially inhibit proliferation (i.e., the surface permits at least 20% doubling in a 24 hour period). Suitable surfaces include tissue culture plastic and surfaces treated with fibronectin. The cells are plated in a suitable medium (e.g., DMEM/F-12, with 10% fetal calf serum) at a density ranging from about $10^6$ to $10^7$, and preferably about 8×106 cells per 100 mm dish. This step of plating on a suitable surface is critical for the proliferation of human progenitor cells, and represents a departure from commonly used techniques for generating rat progenitor cells. Approximately 16–36 hours later, the medium is generally replaced with a suitable growth medium, for instance one which contains N2 supplements and fibroblast growth factor (FGF-2). Preferably, the growth medium also contains epidermal growth factor (EGF), PDGF A/B and/or medium conditioned by perpetualized adult rat hippocampal progenitor cells, as discussed below. For example, a suitable growth medium is DMEM/F-12 with 5 μg/mL insulin, 100 μg/mL transferrin, 20 nM progesterone, 30 nM sodium selenite, 100 μM putrescine and 40 ng/mL human recombinant FGF-2, 40 ng/ML human recombinant EGF, 20 ng/mL human recombinant PDGF A/B and 50% conditioned medium.

Human CNS progenitor cells may be conditionally immortalized by transfection of the plated cells with any suitable vector containing a growth-promoting gene (i.e., a gene encoding a protein that, under appropriate conditions, promotes growth of the transfected cell) such that the production and/or activity of the growth-promoting protein is regulatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

External regulation of the growth-promoting protein may be achieved by placing the growth-promoting gene under the control of an externally-regulatable promoter (i.e., a promoter whose activity may be controlled by, for example, modifying the temperature of the transfected cells or the composition of the medium in contact with the cells). For example, a tetracycline (tet)-controlled gene expression system may be employed (see Gossen et al., *Proc. Natl. Acad. Sci. USA* 89:5547–5551, 1992; Hoshimaru et al., *Proc. Natl. Acad. Sci. USA* 93:1518–1523, 1996). In the absence of tet, a tet-controlled transactivator (tTA) within this vector strongly activates transcription from $ph_{CMV^*-1}$, a minimal promoter from human cytomegalovirus fused to tet operator sequences. tTA is a fusion protein of the repressor (tetR) of the transposon-10-derived tet resistance operon of *E. coli* and the acidic domain of VP16 of herpes simplex virus. Low, non-toxic concentrations of tet (0.01–1.0 μ/mL) almost completely abolish transactivation by tTA.

In a preferred embodiment, the vector further contains a gene encoding a selectable marker (e.g., a protein that confers drug resistance). The bacterial neomycin resistance gene ($neo^R$) is one such marker that may be employed within the present invention. Cells carrying $neo^R$ may be selected by means known to those of ordinary skill in the art, such as the addition of 100–200 μg/mL G418 to the growth medium.

Transfection may be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a progenitor cell culture prepared as described above may be infected after five days in vitro by incubation for about 20 hours in one volume of conditioned medium and two volumes of DMEM/F12 containing N2 supplements such that the final concentrations of additives are 3% fetal calf serum, 20 ng/mL FGF-2 and 4 μg/mL polybrene. Transfected cells carrying a selectable marker may then be selected as described above.

Following transfection, cultures are passaged onto a surface that permits proliferation (i.e., at least 30% of the cells double in a 24 hour period). Preferably, the substrate is a polyornithine/laminin substrate, consisting of tissue culture plastic coated with polyornithine (10 μg/mL) and laminin (10 μg/mL), a polylysine/laminin substrate or a surface treated with fibronectin. Cultures are then fed every 3–4 days with growth medium, which may or may not be supplemented with one or more proliferation-enhancing factors. It has been found, within the context of the present invention, that one or more such factors are necessary for maintenance of conditionally-immortalized CNS progenitor cells. Such proliferation-enhancing factors may be found in medium conditioned by perpetualized adult rat hippocampal progenitor cells (see Gage et al., *Proc. Natl. Acad. Sci. USA* 92:11879–11883, 1995). Such conditioned medium may be prepared by collecting the growth medium from these cells every 3–4 days. Proliferation-enhancing factors may be added to the growth medium when cultures are less than 50% confluent. In a preferred embodiment, the growth medium added to cultures that are less than 50% confluent contains 50% medium conditioned by perpetualized adult rat hippocampal progenitor cells prepared as described above. It will be evident to one of ordinary skill in the art that proliferation-enhancing factors present in such conditioned medium may be identified using standard techniques, and such factors may be added to the growth medium in place of conditioned medium.

The conditionally-immortalized CNS progenitor cell lines may be passaged using standard techniques, such as by trypsinization, when 80–95% confluent. Up to approximately the twentieth passage, it may be beneficial to maintain selection (by, for example, the addition of G418 for cells containing a neomycin resistance gene). Cells may also be frozen in liquid nitrogen for long-term storage.

Clonal cell lines may be isolated from a conditionally-immortalized human CNS progenitor cell line prepared as described above. In general, such clonal cell lines may be isolated using standard techniques, such as by limit dilution or using cloning rings, and expanded. Clonal cell lines may generally be fed and passaged as described above. As discussed in greater detail below, proliferation rate and survival of the clonal cell lines may be enhanced by the addition of epidermal growth factor (EGF) and/or platelet derived growth factor (PDGF), along with FGF-2, to the growth medium.

Conditionally-immortalized human CNS progenitor cell, lines (which may, but need not, be clonal) may generally be induced to differentiate by suppressing the production and/or activity of the growth-promoting protein. For example, if the gene encoding the growth-promoting protein is under the control of an externally-regulatable promoter, the conditions (e.g., temperature or composition of medium) may be modified to suppress transcription of the growth-promoting gene. For the tetracycline-controlled gene expression system discussed above, differentiation may be achieved by the addition of tetracycline to suppress transcription of the growth-promoting gene. In general, 1 μg/mL tetracycline for 4–5 days is sufficient for neuronal and glial morphological differentiation. To promote further differentiation, additional agents may be included in the growth medium. It has been found, within the context of the present invention, that improved differentiation may be achieved in growth medium containing tet, high $K^+$ (e.g., 20 mM), neurotrophin-3 (NT-3, e.g., 50 ng/mL) and brain-derived neurotrophic factor (BDNF, e.g., 50 ng/mL). Other compounds that may be beneficial for differentiation include retinoic acid (e.g., .1 μM), forskolin (e.g., 10 μM) and/or dibutyryl cAMP (e.g., 0.5 mM). The use of such compounds is discussed in greater detail below.

Characterization of both progenitor and differentiated cell lines may generally be performed using techniques well known to those of ordinary skill in the art, including morphological analysis of cell type, immunofluorescence and PCR (to identify cell type-specific markers and receptors, and to confirm the presence of the growth-promoting gene) and electrophysiological analysis of voltage- and ligand-gated currents. Briefly, neuronal cells may be identified morphologically based on the presence of phase bright cell bodies and long, thin processes, whereas astrocytes are characterized by phase-dark cell bodies and wide processes, if present. Neuronal markers include MAP2a/b, tau and neurofilament, and glial markers include GFAP and GalC. The presence or absence of such markers may be readily determined using standard immunofluorescence techniques (employing commercially available primary antibodies and fluorescent reagents) and the levels of mRNA encoding such markers may be determined using PCR or hybridization techniques. Electrophysiological analyses familiar to those of ordinary skill in the art may be employed to evaluate the sodium and calcium currents, as well as ligand-gated currents (e.g., N-methyl-D-aspartate (NMDA), kainate (KA) and γ-amino-n-butyric acid (GABA)), thereby determining the levels of functional channels and receptors. A sodium current of the neuronal form, which is similar to the values obtained for differentiated primary human CNS cultures (see Sah, *J. Neurophysiol.* 74:1889–1899, 1995), may be observed.

The conditionally-immortalized human CNS progenitor cells described herein may contain both neuronal and astrocytic human CNS progenitor cells. Some clonal progenitor cell lines are multi-potent (i.e., can give rise to both neurons and astrocytes). Other progenitor cells specifically generate either neurons or astrocytes upon differentiation. The differentiated cells derived from such cell lines express functional sodium and calcium channels, as well as glutamate and $GABA_A$ receptors in the native environment with intact intracellular signaling pathways.

In certain aspects of the present invention, conditionally-immortalized human CNS progenitor cell lines may be used in a variety of in vitro assays and screens. In one such aspect, the cell lines may be used in in vitro models of neuronal and glial cell death including, but not limited to, neuronal apoptosis induced by growth factor withdrawal and neuronal apoptosis induced by TNFα. Briefly, a clonal neuronal cell line (such as B4, described herein) may be differentiated under conditions designed to minimize the basal level of apoptosis. Suitable conditions may be readily identified by evaluating the percentage of apoptotic nuclei in cells grown under different test conditions. The percentage of apoptotic nuclei may generally be determined by methods well known to those of ordinary skill in the art, such as by DAPI staining or the in situ nick end-labeling assay. Suitable conditions for minimizing basal apoptosis include differentiation in the presence of 1 μg/mL tetracycline, 20 ng/mL NT-3, 20 ng/mL BDNF and 20 ng/mL glial cell-derived neurotrophic factor (GDNF). Cells should be maintained in suitable differentiation conditions for a time sufficient to allow differentiation, while minimizing the basal level of apoptosis (which generally increases during the first 10 days of differentiation). Under the representative conditions described above, about 5–7 days of differentiation is generally optimal, resulting in a culture in which less than about 5% of the cells are apoptotic.

Such differentiated neuronal cells may then be employed in any of several models of apoptosis. In one such model, growth factors and N2 supplement are withdrawn for an amount of time sufficient to significantly increase the percentage of apoptotic cells with condensed nuclei. Preferably, the percentage of such apoptotic cells increases by at least about two fold. Under the representative conditions described above, about 18 hours of withdrawal is generally sufficient. In another model, apoptosis may be induced by the addition of TNFα. A suitable amount of TNFα and exposure time may be readily determined by, for example, evaluating the viability of cells after varying amounts and times. A significant percentage of the cells should be rendered nonviable. Preferably, at least about 50% of the neurons are no longer viable following TNFα treatment. For the representative cells described above, about 1–10 ng/mL TNFα for at least 48 hours is generally sufficient.

Regardless of the particular model, the cells may be used to study the mechanisms of apoptosis, as well as the effect of various conditions and agents on the apoptosis of neuronal cells, using experimental techniques, well known to those of ordinary skill in the art. For example, the cells may be used to screen for an agent that affects CNS cell death. Such a screen may be performed by contacting the cells during growth factor withdrawal or TNFα treatment with a candidate agent and then evaluating the ability of the candidate agent to affect the subsequent level of apoptosis. Similarly, the cells may be used to screen for a protein that regulates CNS cell death. In such a screen, the level of expression or activity of a candidate protein (e.g., an enzyme) is altered within the cells (using standard techniques) and then the affect of the alteration on the level of apoptosis following treatments (including, but not limited to, growth factor withdrawal, TNFα treatment, glutamate addition or β-amyloid addition) is measured.

In another aspect of the present invention, the cell lines described herein may be used within a system for studying protein and/or gene expression in a CNS cell environment. For example, receptor expression and/or activity may be assayed, and the effect of various modifications on such expression and/or activity may be evaluated, using methods well known to those of ordinary skill in the art. In one such method, cell lines may be permanently or transiently transfected with one or more genes of interest such as, but not limited to, genes that produce or modify membrane proteins, secreted proteins or intracellular proteins of interest. Such genes include ion channels, neurotransmitter receptors, β-amyloid and/or MAP kinases. The transfected genes may also be coupled to reporter genes (e.g., luciferase) for use in drug development. Within this and other aspects described herein, conditionally-immortalized human CNS progenitor cells may be employed without differentiation, or differentiated cells may be used. In addition, cells of varying ages and grown in any of a variety of conditions may be employed. The cell lines of the present invention have many advantages over existing cell lines for such studies, including the ability to provide clonal cell lines capable of producing neurons, astrocytes or both and the property of conditional-immortalization, which allows arrest at specific stages of development. The selection of particular cells for any given study will depend on the goals of the study, and those of ordinary skill in the art will be readily able to prepare appropriate CNS cells using the techniques described herein.

In yet another aspect, the differentiated or undifferentiated conditionally-immortalized human CNS cell lines described herein may be used in any of a variety of nucleic acid and/or protein assays. To detect a particular nucleic acid sequence (i.e., DNA and/or RNA) within such CNS cells, the well known methods of PCR and various hybridization techniques may be employed. Such assays may be readily designed and performed using methods described, for example, in Sambrook et al., *Molecular Cloning: A Laboratory Manual*, Cold Spring Harbor Laboratories, Cold Spring Harbor, N.Y., 1989. To detect a protein, the detection reagent is typically an antibody, which may be prepared as described below. There are a variety of assay formats known to those of ordinary skill in the art for using an antibody to detect a protein in a sample. See, e.g., Harlow and Lane, *Antibodies: A Laboratory Manual*, Cold Spring Harbor Laboratory, 1988. Antibodies for use in such assays may be polyclonal or monoclonal. Antibodies may be prepared by any of a variety of techniques known to those of ordinary skill in the art and monoclonal antibodies specific for a protein of interest may be prepared, for example, using the technique of Kohler and Milstein, *Eur. J. Immunol.* 6:511–519, 1976, and improvements thereto.

In a related aspect, the differentiated or undifferentiated conditionally-immortalized human CNS cell lines described herein may be used in any of a variety of screens for agents that modulate the activity of a protein produced by a human CNS cell. Modulation includes the suppression or enhancement of the activity of the protein of interest. Such modulation may occur at the transcriptional or translational level, or may be the result of altering the activity of the intact protein. Modulation of protein activity may be direct (i.e., the modulating agent may interact directly with the protein of interest) or may be indirect (i.e., the modulating agent may alter the expression and/or activity of one or more other proteins which in turn modulate the activity of the protein of interest). Modulating agents may be antibodies (e.g., monoclonal), polynucleotides or other drugs. Agents that modulate the activity of any cellular protein may be identified within such screens. In particular, modulating agents may be identified for proteins such as neurotransmitter receptors (e.g., AMPA-preferring receptors, kainate receptors, GABA receptors, adenosine receptors and/or 5-HT receptors), growth factor receptors (e.g., receptors for FGF-2, EGF, BDNF, NT-3, GDNF and/or TNFα) or ion channels (e.g., sodium channels, calcium channels and/or potassium channels).

In general, modulating agents may be identified by contacting a CNS cell as described herein with a test compound, and evaluating the effect of the test compound on the level or activity of the protein of interest using standard techniques, such as PCR or hybridization (for evaluating levels of mRNA) or any of a variety of immunoassays or functional assays appropriate for the protein of interest. For example, calcium-sensitive or voltage-sensitive dye coupled assays, cAMP measurements and/or receptor binding assays may be employed to evaluate the effect of a candidate modulating agent. In general, a suitable amount of antibody or other agent for use in such a screen will vary depending on the particular protein, but will range from about 10 μg to about 100 mg.

In a further aspect, the human CNS progenitor cell lines described herein may be used in the identification of novel genes and proteins present in human CNS cells. Conventional or newer techniques, such as PCR, differential display, hybridization, expression library screens, immunoassays and two-hybrid screens may be employed for such identification. A particularly useful technique is differential gene screening. The clonal CNS cell lines described herein are particularly suited to such studies because they are derived from a single parental cell and, therefore, CNS cell-specific genes are amplified with respect to non-clonal cell lines. Novel genes and proteins that are expressed upon experimental manipulation (e.g., induction of apoptosis) may also be identified.

Conditionally-immortalized human CNS progenitor cell lines of the present invention may also be used in assays to detect the presence or absence of a particular protein in a sample. In general, an assay may be performed by contacting CNS progenitor cells with a sample and then measuring a response induced by the protein within the cells using methods familiar to those of ordinary skill in the art. For example, a response may be measured using differential display techniques.

In other aspects, the human CNS progenitor cell lines described herein may be used in vivo, in transplantation studies and for treatment of a patient. For example, cells may be introduced by intracerebral grafting into animals such as rats, mice or monkeys. Studies may address the differentiation of the cells when transplanted into the developing or adult CNS. The ability of the cells to serve as therapeutic agents in pathological conditions can also be examined. In particular, the cells themselves may have the capacity to functionally replace neurons that die in neurodegenerative disorders or may serve as sources of agents (such as trophic factors) that have therapeutic benefit. Such agents may be produced by endogenous genes or by genes transfected into the cells.

For treatment of a patient, conditionally-immortalized human CNS progenitor cells and/or modulating agents (as described above) may be administered to a patient (either prophylactically or for treatment of an existing disease). Diseases that may be prevented and/or treated using human CNS progenitor cells and/or modulating agents include, but are not limited to, pathological conditions where neurons have degenerated, such as Alzheimer's disease, Parkinson's disease, amyotrophic lateral sclerosis, stroke and/or traumatic head injury. Cells may be introduced by, for example, stereotaxic implantation or intracerebral grafting into the CNS of patients. The cells themselves may have the capacity to functionally replace neurons that die in neurodegenerative disorders, or may serve as sources of agents (such as trophic factors) that have therapeutic benefit. Modulating agents may be administered by any of a variety of routes known to those of ordinary skill in the art. Such agents may be administered in their active form, as prodrugs (i.e., compounds that are converted to the active form within the patient) or as nucleic acid sequences encoding the modulating agent or prodrug. CNS progenitor cells for use in this aspect of the present invention may, but need not be, further transfected such that they express one or more additional proteins (such as modulating agents) within the patient.

For administration to a patient, one or more human CNS progenitor cells (and/or modulating agents) are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Any suitable carrier known to those of ordinary skill in the art may be employed in the pharmaceutical compositions of the present invention. The selection of a carrier will depend, in part, on the nature of the substance (i.e., cells or chemical compounds) being administered. Representative carriers include physiological saline solutions, gelatin, water, alcohols, natural or synthetic oils, saccharide solutions, glycols, injectable organic esters such as ethyl oleate or a combination of such materials. Optionally, a pharmaceutical composition may additionally contain preservatives and/or other additives such as, for example, antimicrobial agents, anti-oxidants, chelating agents and/or inert gases, and/or other active ingredients.

Routes and frequency of administration, as well doses, will vary from patient to patient and on the nature of the substance being administered. In general, the pharmaceutical compositions may be administered intravenously, intramuscularly, subcutaneously or intracavity. Doses are preferably administered daily. A suitable dose is an amount that is sufficient to show improvement in the symptoms of a patient afflicted with a disease of the CNS or to inhibit the onset of such a disease. Such improvement may be detected based on improvement and/or delay in clinical symptoms associated with the disease. In general, the amount of modulating agent present in a dose, or produced in situ by DNA present in a dose, ranges from about 1 mg to about 200 mg per kg of host. Suitable dose sizes will vary with the size of the patient, but will typically range from about 0.1 mL to about 5 mL for 10–60 kg animal.

The following Examples are offered by way of illustration and not by way of limitation.

EXAMPLES

Example 1

Preparation and Characterization of Human CNS Progenitor Cell Lines

This Example illustrates the preparation of a representative conditionally-immortalized human CNS progenitor cell line.

A. Primary Cell Culture

Proliferating primary cultures of human fetal CNS progenitor cells were established from whole human fetal brain tissue of 13 weeks gestational age, which was obtained through Advanced Bioscience Resources, Inc. (Alameda, Calif.). The tissue was procured in compliance with state and federal laws and regulations, including those set forth by the Uniformed Anatomical Gift Act and National Organ Transplant Act, and appropriate consent forms were used. Brain tissue fragments were kept for approximately 24 hours at 4° C. in Hank's balanced salt solution (with no calcium or magnesium) containing penicillin (50 I.U./mL) and streptomycin (50 μg/mL) before dissociation.

The tissue was dissociated enzymatically and maintained in culture for 5 days before retroviral infection. Enzymatic incubation was carried out for 6 minutes at 37° C. with gentle agitation in 3 mg/mL protease (Sigma Type XXIII, Sigma Chemical Co., St. Louis, Mo.) in calcium and magnesium-free Hank's. Following enzymatic incubation, the tissue was washed with warm calcium and magnesium-free Hank's, and then with warm enzyme inhibitor. The enzyme inhibitor consisted of trypsin inhibitor (1 mg/mL) and bovine serum albumin (1 mg/mL). Brain tissue fragments were triturated approximately 15 times with a 10 mL pipette, and then spun at 1000 rpm for 3 minutes. The resulting pellet was resuspended in 1 mL of DMEM/F-12, with 10% fetal calf serum, and triturated with pipettes of decreasing bore size to yield a single-cell suspension. Cells were plated on tissue culture plastic in DMEM/F-12 with 10% fetal calf serum, at a density of $8 \times 10^6$ cells per 100 mm dish. Approximately 24 hours later, the medium was replaced with growth medium consisting of DMEM/F-12 with N2 supplements (5 μg/mL insulin, 100 μg/mL transferrin, 20 nM progesterone, 30 nM sodium selenite, and 100 μM putrescine) and FGF-2 (human recombinant, 40 ng/mL).

B. Immortalization

For immortalization, a retroviral vector (LINXv-myc) was used in which the v-myc oncogene is transcribed in a tet-regulated fashion (see Hoshimaru et al., *Proc. Natl. Acad. Sci. USA* 93:1518–1523, 1996). For selection of the transfected cells, a gene conferring neomycin resistance is also cloned into the vector. Progenitor cell cultures (5 days in vitro) were infected by incubation for about 20 hours with a mixture of one volume of the conditioned medium collected from the producer cell line for LINXv-myc and two volumes of DMEM/F12 containing N2 supplements. The final concentrations of additives were 3% fetal calf serum, 20 ng/mL FGF-2 and 4 μg/mL polybrene. Cultures were then selected with 200 μg/mL G418. If the cultures were less than 50% confluent, then they were fed growth medium containing conditioned medium (CM). Growth medium containing CM consisted of DMEM/F-12 with N2 supplements, FGF-2 (human recombinant, 20–40 ng/mL) 50% medium conditioned by perpetualized adult rat hippocampal progenitor cells (i.e., growth medium collected from the cells every 3–4 days. For clonal cell lines, as discussed below, growth medium also contained (in some cases, noted below) EGF (human recombinant, 40 ng/mL) and PDGF A/B (human recombinant, 20 ng/mL).

C. Expansion and Passaging of Immortalized Cultures

After retroviral infection, cultures were passaged onto a polyornithine/laminin substrate, consisting of tissue culture plastic coated with polyornithine (10 μg/mL) and laminin (10 μg/mL), and fed every 3–4 days with growth medium with (<50% confluency) or without (>50% confluency) CM. Up to passage ~20, 100–200 μg/mL G418 was included in the growth medium approximately every other feeding. Cultures were passaged by trypsinization when 80–95% confluent. Typically, cultures were split 1:3, resulting in about 5 to $25 \times 10^3$ cells seeded per $cm^2$. To freeze cells for long-term storage in liquid nitrogen, cultures were trypsinized and resuspended in N2 medium containing FGF-2, 10% DMSO and, in some cases, 50% heat-inactivated fetal bovine serum.

By day 10 in vitro, a significant amount of cell death had occurred, and colonies began to appear. The culture was then switched to growth medium containing CM. By day 18 in vitro, only distinct colonies remained. These colonies consisted of about 20–40 flat, phase-dark polygonal cells, with no processes or short processes. Morphologies were homogeneous within a colony, and varied slightly between colonies. Approximately 10 colonies were present on a 100 mm dish, indicating that about 1 of $10^6$ cells initially seeded had been successfully immortalized.

In the proliferative growth condition, the immortalized cells exhibited a mean doubling time of 48 hours (based on cell counts, data not shown) and have surpassed 85 doublings. To further assess proliferation as well as incorporation of the oncogene, immortalized human fetal CNS cells were labeled for bromodeoxyuridine (BrdU) and v-myc. Cultures were processed for immunohistochemistry 3–11 days after passaging. Cells were fixed for 10–30 min with 4% paraformaldehyde (for most antigens), in methanol (for v-myc), or in 4% paraformaldehyde followed by 2N HCl and then 0.1 M sodium borate (for BrdU). For immunofluorescence staining, the cells were then incubated sequentially with the primary antibody in PBS containing 10% donkey serum and 0.25% Triton X-100 overnight at 4° C. followed by fluorescein-conjugated or Texas red-conjugated secondary antibody (Jackson Immunoresearch Laboratories, Inc., West Grove, Pa.) used at 1:500 for 1 hour at room temperature. The cultures were rinsed and coverslipped with Vectashield (Vector Laboratories, Burlingame, Calif.) before scoring and photographing representative fields. Primary antibodies used for immunofluorescence were polyclonal antibodies against v-myc (Caltag, Burlingame, Calif.) and monoclonal antibodies against BrdU (Boehringer Mannheim, Indianapolis, Ind.).

As shown in FIG. 1, almost all cells incorporated BrdU when grown in the proliferative condition. In contrast, after addition of tetracycline (Tc), only 11% of cells stained for BrdU. Substantial nuclear staining for v-myc was present in the proliferative growth condition, and the level of staining decreased in intensity after addition of tetracycline. These data show that the cells contain the v-myc oncogene, and that tetracycline suppresses expression of the oncoprotein and proliferation.

Example 2

Differentiation of Human CNS Progenitor Cell Lines

This Example illustrates the preparation of differentiated CNS cells from the human CNS progenitor cell line described in Example 1, and the characterization of the differentiated cells.

A. Differentiation of Immortalized Cultures

Figure 2:
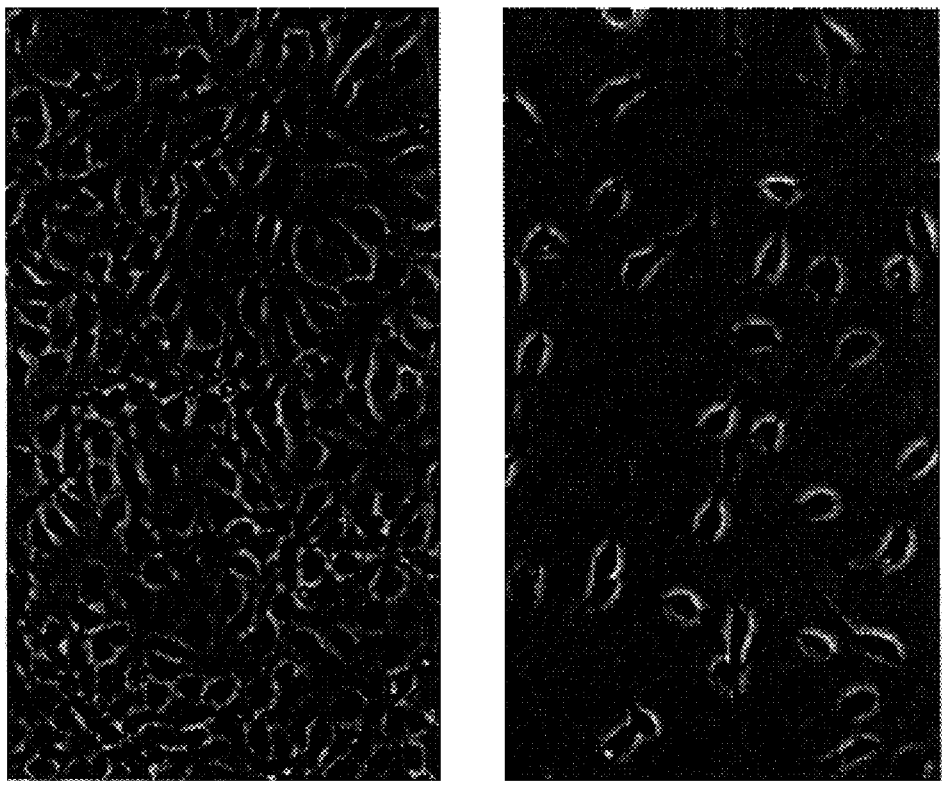
FIG. 2 is a photograph of a representative human CNS progenitor cell line (B4) after 7 days of culture in the absence (left panel) or presence of tetracycline and retinoic acid for 1 day, followed by tetracycline, high $K^+$, NT-3 and BDNF for 6 days (right panel).

To differentiate the immortalized cells, cultures (clone B4, described below) were switched to DMEM/F12 containing N2 supplements and tetracycline (1 μg/mL to suppress transcription of the oncogene). After approximately 7 days of tet addition (tet+RA for 1 day, followed by tet, high $K^+$, NT-3 and BDNF for 6 days) neuronal and glial morphological differentiation occurred (FIG. 2, right panel). Phase-bright cells with long, thin processes were present (suggestive of neuronal morphology), as well as larger phase-dark cells with wider processes (suggestive of astrocyte morphology). In the proliferative growth condition (FIG. 2, left panel), cells exhibited progenitor cell morphology (small phase-dark cells, with polygonal shape, and very short processes, if present).

Immortalized Human CNS Progenitor Cultures Differentiate into Neurons and Astrocytes. To determine whether the immortalized human fetal cells expressed cell type-specific markers after differentiation, cultures were immunolabeled for the neuronal markers MAP2a/b, tau and neurofilament (200 kD), and the glial markers GFAP and GalC. Immunofluorescence staining was performed as described in Example 1 except that the cells were fixed for 10–30 minutes with 4% paraformaldehyde in PBS. The primary antibodies against MAP2a/b, neurofilament, GFAP and GalC were obtained from Chemicon (Temecula, Calif.). Primary antibodies against tau were obtained from Boehringer Mannheim (Indianapolis, Ind.). For immunoperoxidase staining, cells were incubated with the primary antibody in PBS containing 10% donkey serum and 0.25% Triton X-100 overnight at 4° C., and then with biotin-conjugated goat anti-rabbit IgG or horse anti-mouse IgG antibodies (Vector Laboratories, Burlingame, Calif.) for 1 hour at room temperature followed by 1 hour treatment with a pre-formed mixture of avidin-biotinylated horseradish peroxidase complex (Vectastain Elite ABC kit, Vector Laboratories, Burlingame, Calif.). The reaction products were visualized with diaminobenzidine histochemistry. Primary polyclonal antibodies used for immunoperoxidase staining of GluR1, GluR2/3, GluR4 were obtained from Chemicon (Temecula,. Calif.), and monoclonal antibodies against NMDAR1 and GluR5/6/7 were obtained from Pharmingen (San Diego, Calif.).

Figure 3A:
FIGS. 3A and 3B are photographs showing the result of immunofluorescence staining of representative immortalized human CNS progenitor cells for the neuronal marker MAP2a/b (FIG. 3A) and the astrocytic marker GFAP (FIG. 3B), after growth in tetracycline for 6 days. The calibration bar represents 20 µm.
Figure 3B:
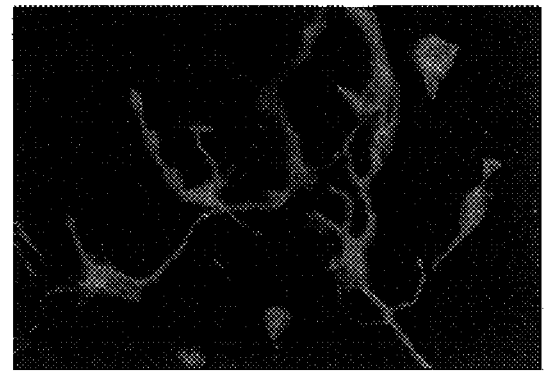
Figure 4A:
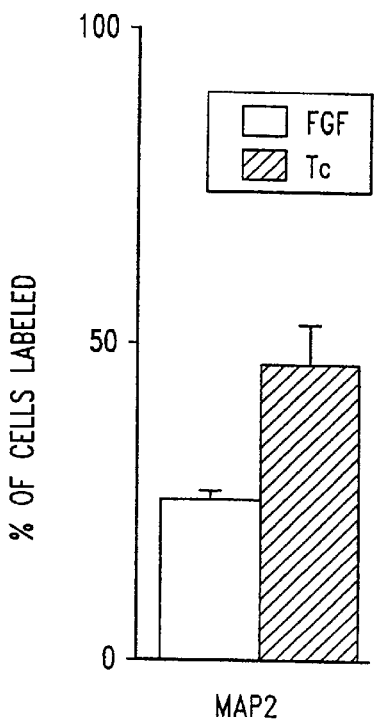
FIGS. 4A, 4B and 4C are histograms showing the percentage of representative immortalized human CNS progenitor cells labeled with antibodies against MAP2 (FIG. 4A), GFAP (FIG. 4B) and NMDAR1, GluR1, GluR2/3 and GluR5/6/7 (FIG. 4C). In each case, the percentage of cells labeled before (white bars) and after (dark bars) culturing in the presence of tetracycline for 6 days is shown.
Figure 4B:
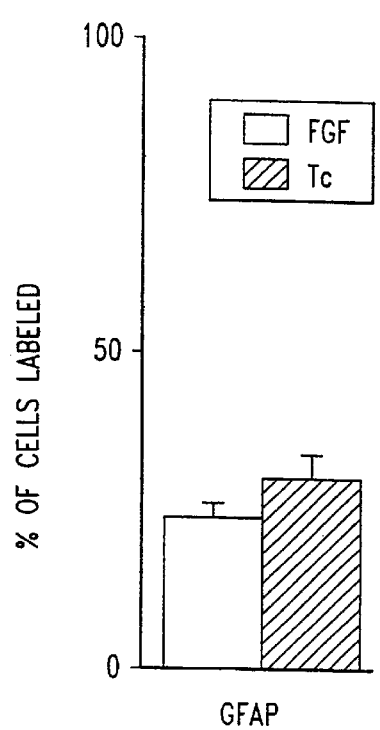
Figure 4C:
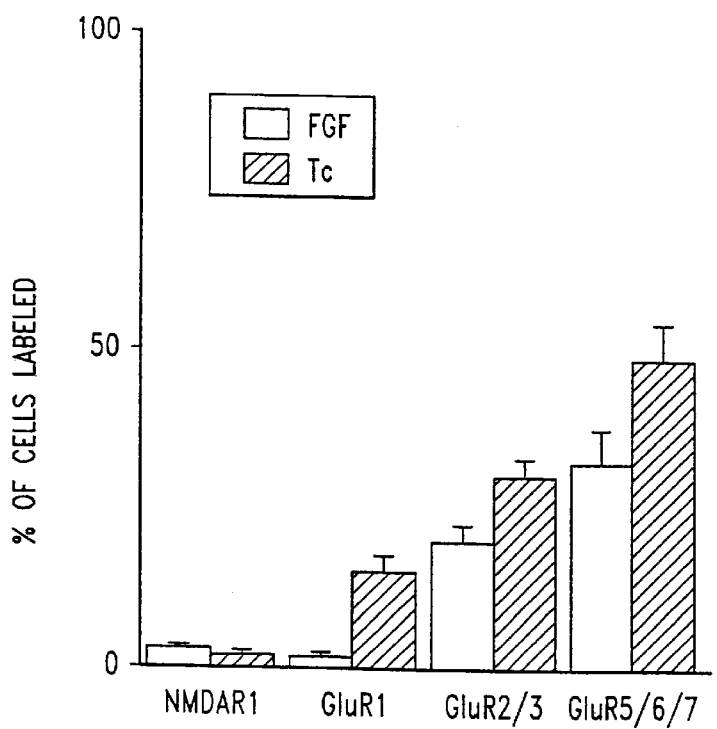

Staining was weak before and after differentiation for the mature neuronal markers tau and neurofilament (200 kD) and the oligodendrocyte marker, GalC. However, staining for the earlier neuronal marker, MAP2a/b, and the astrocytic marker, GFAP, was present to a significant extent. After growth in tet (1 µg/mL, 5–6 days), the percentage of MAP2a/b-positive cells doubled to ~50%, whereas the percentage of GFAP-positive cells increased slightly, to ~30% (FIGS. 3 and 4). MAP2a/b-positive cells exhibited neuronal morphology, and GFAP-positive cells exhibited astrocytic morphology. These two populations of cells were non-overlapping in double-labeling experiments. These results indicate that both neuronal and astrocytic human CNS progenitors were immortalized.

Immortalized Human CNS Progenitor Cells Express Functional Sodium and Calcium Channels after Differentiation. After growth in tet for about 1 week, immortalized human fetal CNS cells exhibited very little sodium or calcium current. To promote further differentiation, cells were grown for about 2 weeks with additional agents, such as tet+20 mM KCl+NT-3 (50 ng/mL)+BDNF (50 ng/mL), tet+RA (retinoic acid, 1 µM), tet+FSK (forskolin, 10 µM), tet+dbcAMP (dibutyryl cAMP, 05 mM), tet+PMA (phorbol 12-myristate 13-acetate, 20 nM), and tet+human serum (10%). The results are presented in Table 1. After growth with tet, high $K^+$, NT-3 and BDNF; tet and RA; tet and FSK, or tet and dbcAMP, a subset of cells differentiated morphologically by extending long, thin processes. These cells were chosen for subsequent electrophysiological characterization. In contrast, after growth with tet and PMA, or tet and human serum, no cells of neuronal morphology remained. In subsequent experiments discussed below, the concentrations of the following agents in the growth medium (where indicated) were: retinoic acid (0.5–10 µM), dibutyryl cAMP (0.5–1 mM), forskolin (10–50 µM), phorbol esters (5–50 nM phorbol 12-myristate 13-acetate,), high $K^+$ (20 mM), NT-3 (20–50 ng/mL), BDNF (20–50 ng/mL), GDNF (20–50 ng/mL) and/or human serum (10%).

TABLE 1

Immortalized Human Fetal CNS Progenitor Cells: Effects of Growth Conditions

| Growth Condition | Neuronal Differentiation |
| --- | --- |
| FGF-2 | − |
| Tet + high $K^+$ + NT-3 + BDNF | ++ |
| Tet + RA | +/++ |
| Tet + FSK | + |
| Tet + dbcAMP | (+)/+ |
| Tet + PMA | − |
| Tet + Human Serum | − |

Cultures were used for electrophysiology 2–13 days after passaging. The whole-cell configuration of the patch clamp technique was used to study voltage- and ligand-gated currents. Pipettes (2–5 MΩ resistance) were pulled from Boralex glass (DynalabCorp., Rochester, N.Y.) and, in most cases, coated with Sylgard (Dow Coming Corp., Midland, Mich.) and fire-polished. They were filled with internal solution containing 108 mM cesium-methanesulfonate, 4 mM $MgCl_2$, 9 mM EGTA (ethylene glycol bis(b-aminoethyl ether)-N,N,N',N'-tetraacetic acid), 9 mM HEPES (4-(2-hydroxyethyl)-1-piperazineethanesulfonic acid), 4 mM ATP, 14 mM creatine phosphate (Tris salt), 0.3 mM GTP (Tris salt), and, in most cases, 50 U/mL creatine phosphokinase, pH 7.4 with CsOH. Whole-cell recordings were initially established in the bath solution (Tyrode's: 150 mM NaCl, 4 mM KCl, 2 mM $MgCl_2$, 10 mM glucose, 10 MM HEPES, pH 7.4 with NaOH; 2 mM $CaCl_2$ and 4 mM $BaCl_2$ added). Sodium currents were characterized in this bath solution, or in 160 mM NaCl, 2 mM $CaCl_2$, and 10 mM HEPES, pH 7.4 with NaOH. Calcium currents were assessed by using the following external solution: 160 mM TEA-Cl, 5 mM $BaCl_2$, and 10 mM HEPES, pH 7.4 with TEA-OH, 1 µM tetrodotoxin (TTX, Sigma, St. Louis, Mo.) added. Responses to NMDA (Sigma, St. Louis, Mo.) plus glycine (Fisher, Pittsburgh, Pa.), kainate (Sigma, St. Louis, Mo.) and GABA (RBI, Natick, Mass.) were elicited by applying agonist in the following external solution: 160 mM NaCl, 2 mM $CaCl_2$, 0.1–1 mM EDTA, 1 µM TTX, and 10 nM HEPES, pH 7.4 with NaOH. External solutions flowed from an array of microcapillary tubes (internal diameter 140 mm), driven by gravity. Drugs were applied by moving the array of tubes, and solution exchange was complete in less than a second. All drug stocks were stored frozen, and diluted into external solution on the day of the experiment.

Whole-cell currents were recorded using an Axopatch 200A patch clamp amplifier, and the BASIC-FASTLAB interface system (INDEC Systems, Capitola, Calif.). Voltage-dependent currents were filtered at 10 KHz (4-pole Bessel low-pass) and digitized every 25 µs (sodium current) or 50 µs (calcium current). Ligand-gated currents were filtered at 1 or 10 KHz and digitized every 50 ms. Series resistance compensation was employed, typically for 80–95% of the series resistance measured from the uncompensated capacity transient (dividing the decay time constant by cell capacitance) or from the potentiometer used for nulling the capacity transient. Data were accepted for sodium current only if the remaining voltage error (calculated as current times uncompensated series resistance) was less than 1 mV, and if voltage control was adequate as judged by a graded increase in peak current as test depolarizations were increased. For calcium and ligand-gated currents, uncompensated voltage errors were less than 5 mV. Reported potentials have been corrected for a liquid junction potential of −10 mV between the internal solution and the Tyrode's solution in which the pipette current was zeroed before sealing onto the cell. Sodium and calcium channel currents were corrected for leak and capacitative currents by subtraction of an appropriately scaled current elicited by a hyperpolarization from −80 mV to −90 mV. All experiments were done at 21–25° C. Statistics are given as mean+SEM.

Figure 5A:
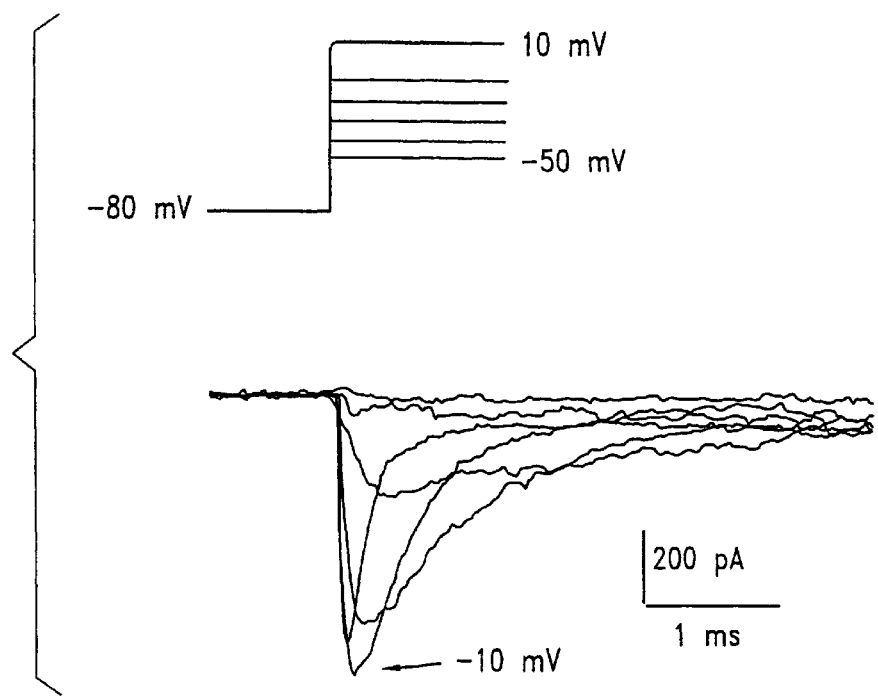
FIGS. 5A and 5B depict the results of electrophysiological analysis of voltage-dependent sodium current in a representative immortalized human CNS progenitor cell after differentiation. The cell was maintained at a holding potential of −80 mV and depolarized to test potentials ranging from −75 mV to +85 mV. Current traces are shown in FIG. 5A, and the peak current-voltage relationship is shown in FIG. 5B.
Figure 5B:
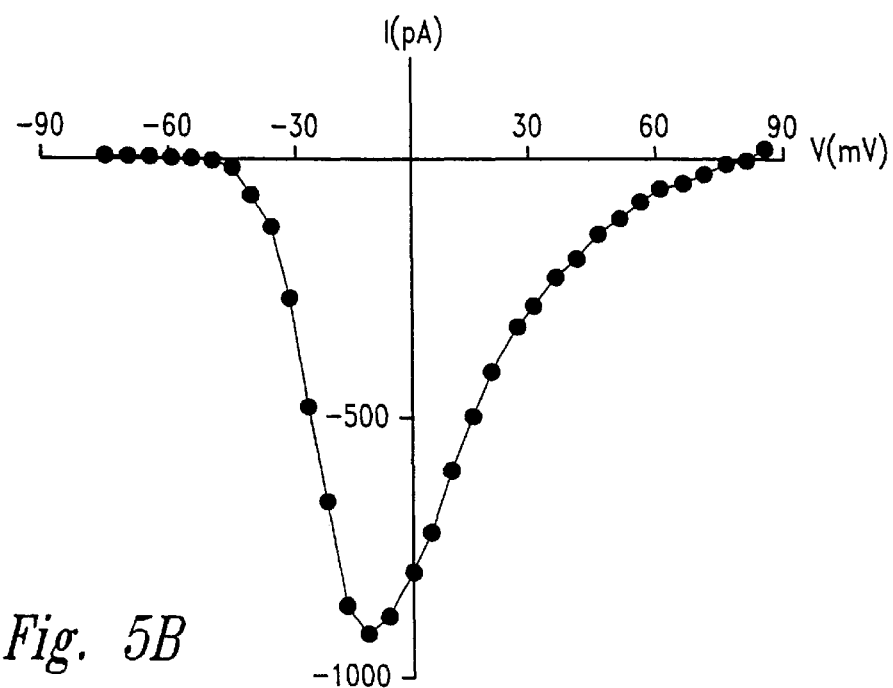
Figure 6A:
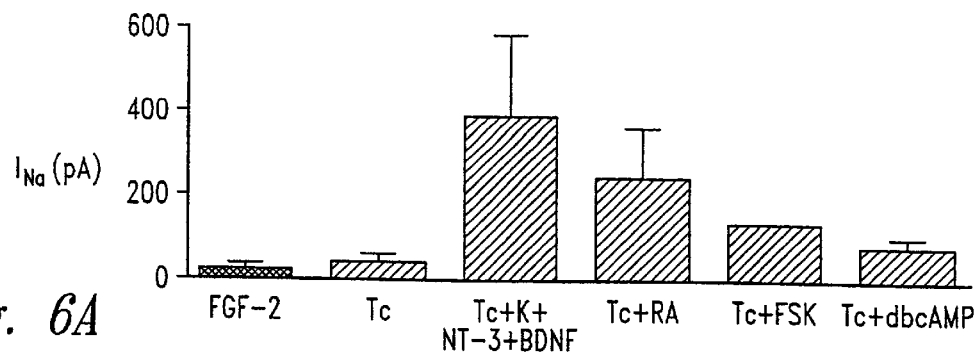
FIGS. 6A, 6B, 6C and 6D are histograms showing the effect of varying differentiation conditions on voltage- and ligand-gated currents in representative immortalized human CNS progenitor cells.
Figure 6B:
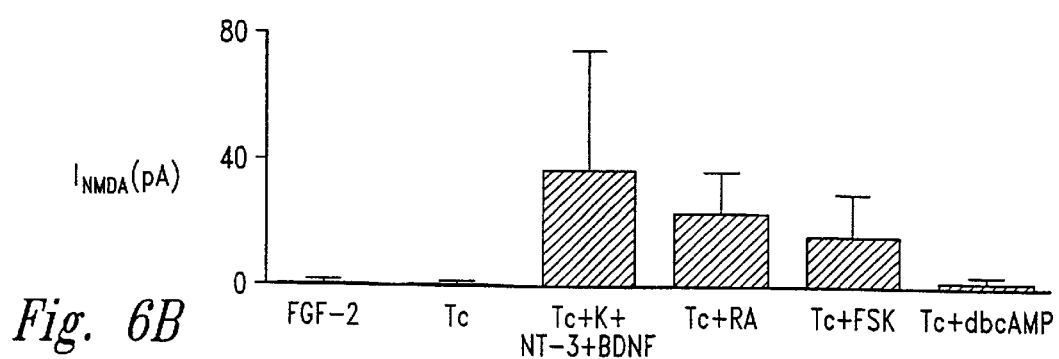
Figure 6C:
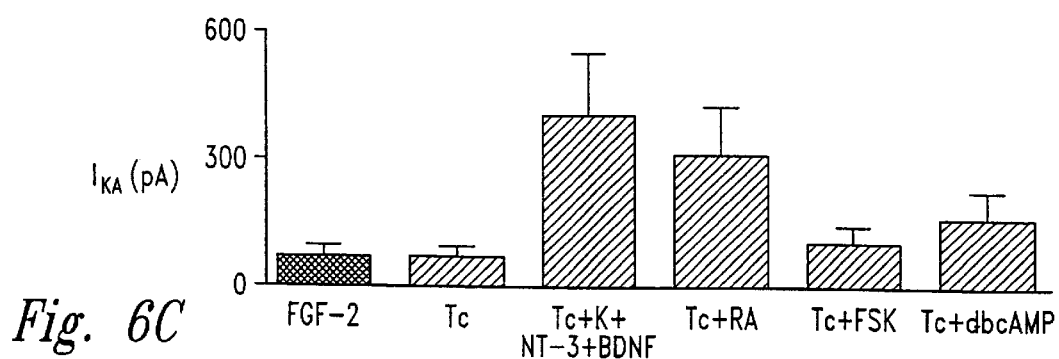
Figure 6D:
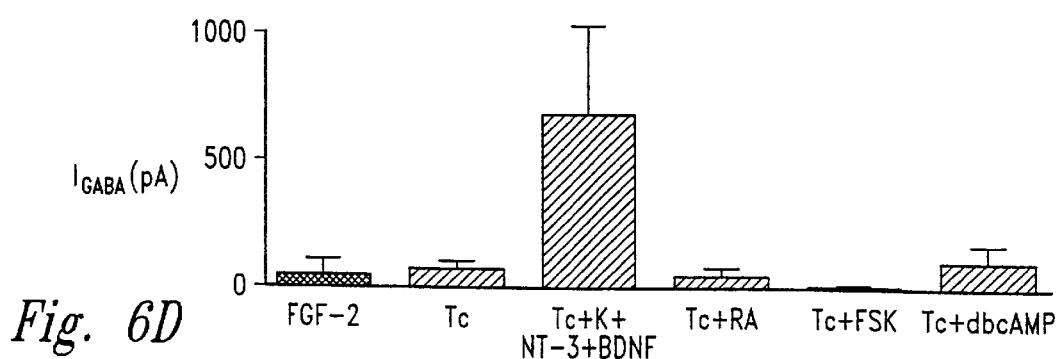

Based on electrophysiological experiments, medium containing tet, high $K^+$, NT-3 and BDNF appears to be optimal for differentiation, whereas the addition of tet and RA may also be useful for restoring voltage-gated currents. Sodium currents (FIGS. 5 and 6) were restored to ~50% of that in primary differentiated human fetal CNS neurons, whereas high-voltage activated calcium currents remained small, averaging 27±9 pA (10 cells). Moreover, the restored sodium current was of the neuronal form, exhibiting a midpoint of inactivation of −56±2 mV and a slope factor of 7±1 mV (7 cells), similar to values obtained for differentiated primary human CNS cultures.

Figure 7:
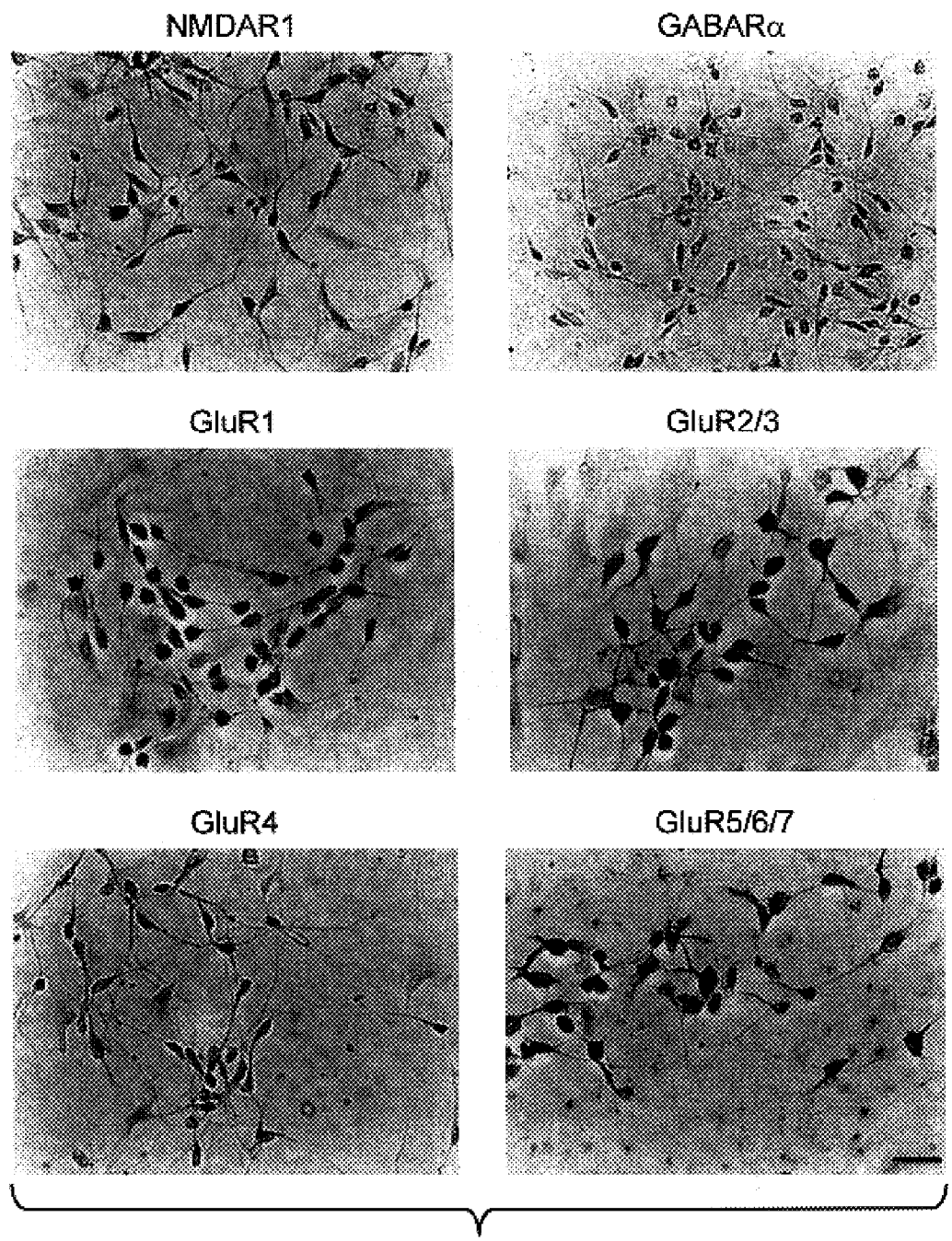
FIG. 7 is a photograph showing the results of immunoperoxidase staining of representative immortalized human CNS progenitor cells (cultured in the presence of tetracycline for 1 week) for the receptor subunits NMDAR1, GluR1, GluR2/3, GluR4, GluR5/6/7 and GABARα, as indicated.

Immortalized Human CNS Progenitor Cells Express Glutamate and $GABA_A$ Receptors after Differentiation. To determine if neurotransmitter receptors might be present, immortalized human CNS lines were stained for the following receptor subunits as described above: NMDAR1, GluR1, GluR2/3, GluR4, GluR5/6/7 and GABARα (Chemicon, Temecula, Calif.) (FIG. 7). After growth in tet for 6 days, there were substantial increases in the percentages of cells that were positive for GluR1, GluR2/3 and GluR5/6/7 (FIG. 4), whereas staining for NMDAR1, GluR4 and GABARα was still low. The significant amount of staining for GluR1, GluR2/3 and GluR5/6/7 suggested that AMPA-preferring and kainate receptors were present.

Figure 8A:
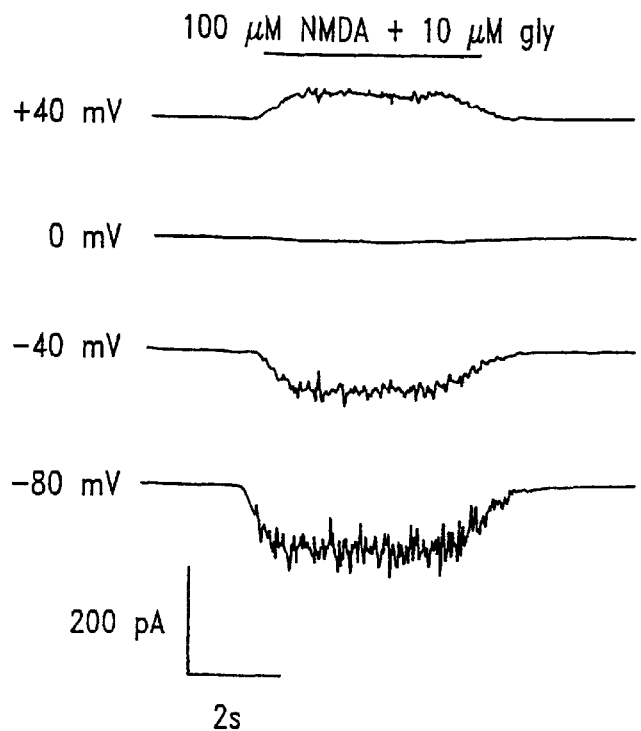
FIGS. 8A and 8B depict the results of electrophysiological analysis of NMDA-gated current in representative immortalized human CNS progenitor cells differentiated by growth in medium containing tet, high $K^+$, NT-3 and BDNF. Currents in FIG. 8A were elicited by agonist application (indicated by the bar) at the different holding potentials shown. The current-voltage relationship for these responses is shown in FIG. 8B.
Figure 8B:
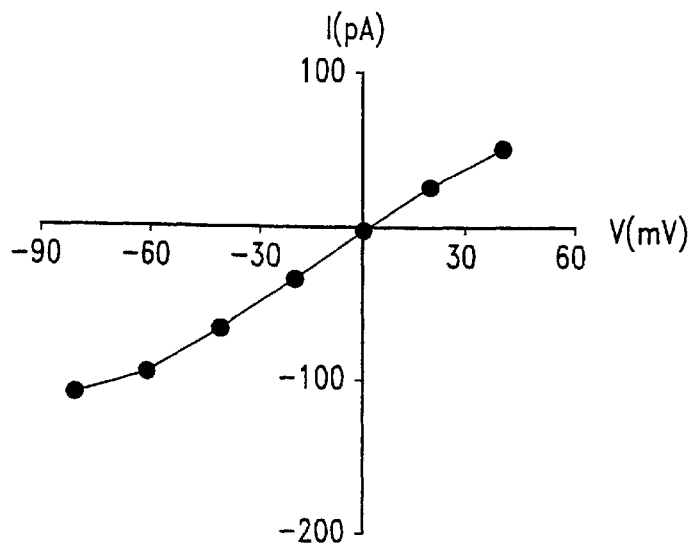
Figure 9A:
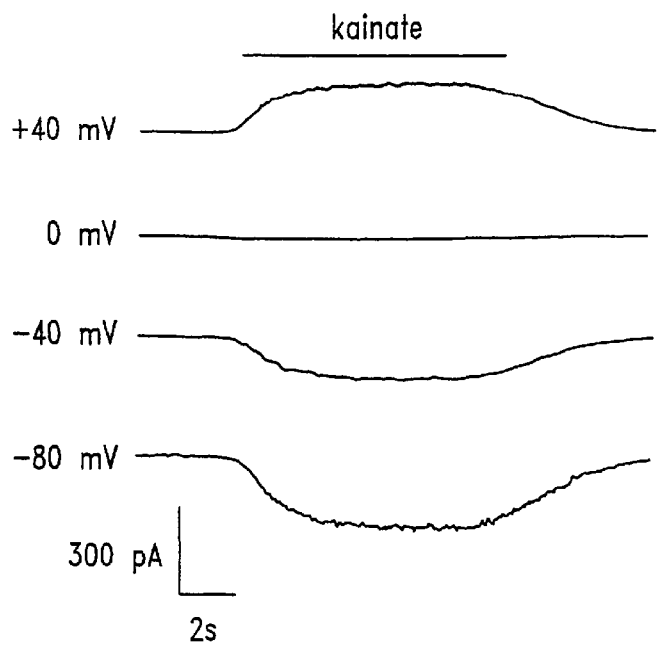
FIGS. 9A and 9B depict the results of electrophysiological analysis of kainate-gated current in representative immortalized human CNS progenitor cells differentiated by growth in medium containing tet and RA. Currents in FIG. 9A were elicited by agonist application (indicated by the bar) at the different holding potentials shown. The current-voltage relationship for these responses is shown in FIG. 9B.
Figure 9B:
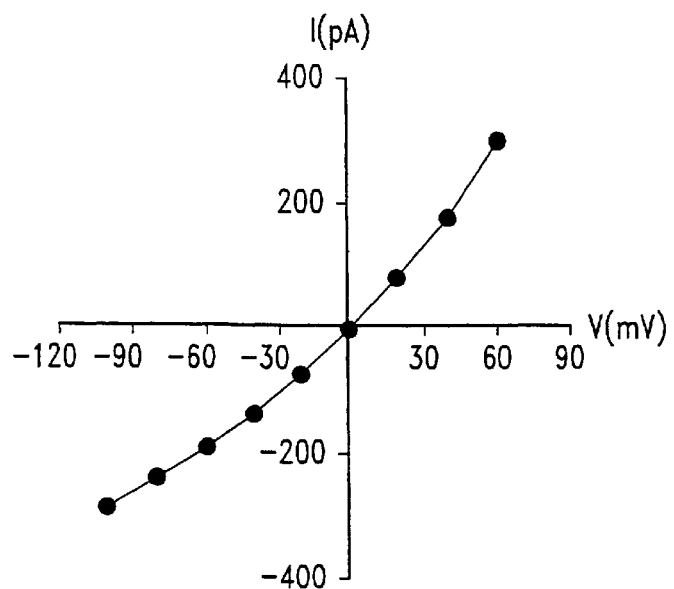
Figure 10A:
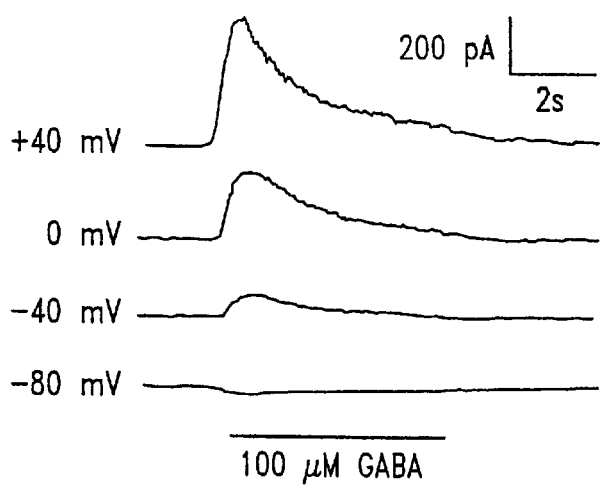
FIGS. 10A and 10B depict the results of electrophysiological analysis of GABA-gated current in representative immortalized human CNS progenitor cells differentiated by growth in medium containing tet and dbcAMP. Currents in FIG. 10A were elicited by agonist application (indicated by the bar) at the different holding potentials shown. The current-voltage relationship for these responses is shown in FIG. 10B.
Figure 10B:
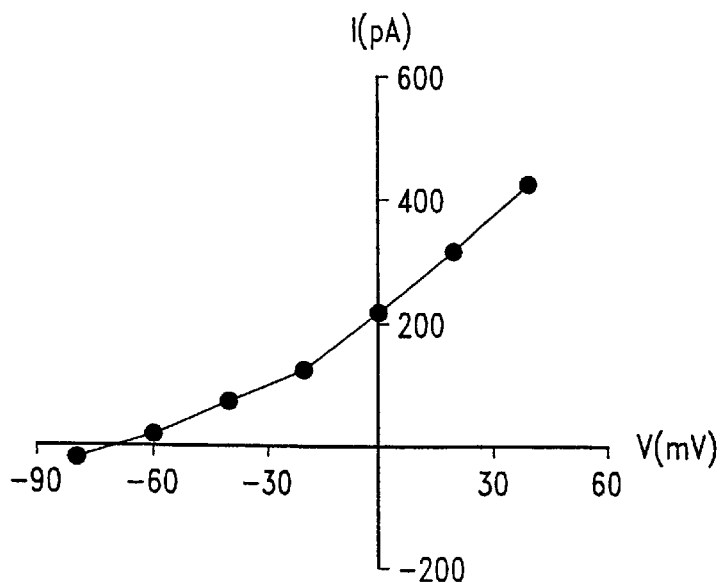

Although immunoperoxidase staining suggested that 20–50% of cells should respond to kainate after growth in tet, immortalized human fetal CNS cells exhibited little or no ligand-gated current after growth in tet or proliferative conditions. However, if cells were grown with additional differentiating agents for about 2 weeks, ligand-gated currents increased substantially (FIG. 6). As with sodium current, the best conditions for restoring ligand-gated currents were medium containing tet; high $K^+$, NT-3 and BDNF and medium containing tet and RA. Agents that increased cAMP up-regulated ligand-gated responses to the smallest extent. After growth with tet, high $K^+$, NT-3 and BDNF, or tet and RA, NMDA responses (FIG. 8) were present in one-third of cells sampled, and kainate (FIG. 9) currents were restored to levels similar to that in primary, non-proliferating cultures (data not shown). GABA responses (FIG. 10), however, were up-regulated after growth with tet+high $K^+$+NT-3+BDNF, but not tet+RA. Kainate current-voltage relationships were linear or outwardly rectifying in 5/6 cells, and reversed at 1±2 mV. In 1 cell, the current-voltage relationship was inwardly rectifying, and reversed at 16 mV, consistent with a significant calcium permeability. The restoration of NMDA current establishes that the immortalized human CNS cells can be differentiated into neurons, because NMDA responses are found exclusively in neurons.

Example 3

Preparation and Characterization of Clonal Human CNS Progenitor Cell Lines

This Example illustrates the generation of clonal human CNS progenitor cell lines, and the characterization of such cell lines.

A. Isolation of Clonal Cell Lines

Clones were isolated from the human CNS progenitor cell line described in Example 1 by limit dilution in 96-well plates. Clones were fed and passaged as above. Of the distinct clonal cell lines generated, four are described in detail below and are referred to herein as clones B4, C2, E5 and C10.

Figure 11A:
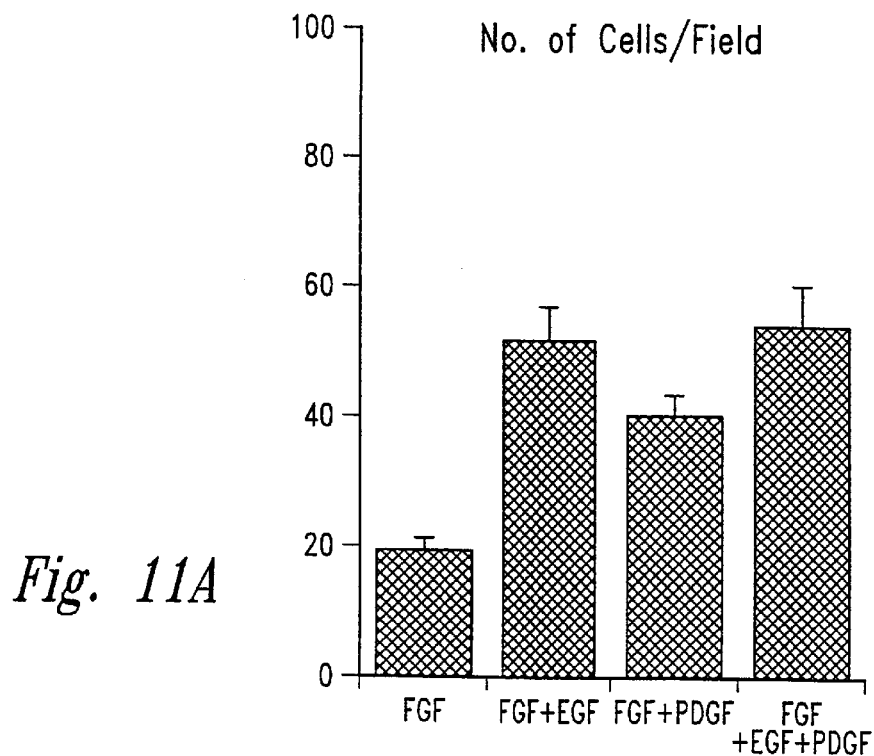
FIGS. 11A and 11B are histograms showing the number of cells per field (FIG. 11A) and the percent of cells labeled by BrdU (FIG. 11B) for a representative human clonal CNS progenitor cell line (C2) following culture in the presence of FGF-2 (column 1), FGF-2 and EGF (column 2), FGF-2 and PDGF A/B (column 3) or FGF-2, EGF and PDGF A/B (column 4). In each case, the level of FGF-2 was 40 ng/mL. When added, the level of human recombinant EGF was 40 ng/mL and the level of human recombinant PDGF A/B was 20 ng/mL.
Figure 11B:
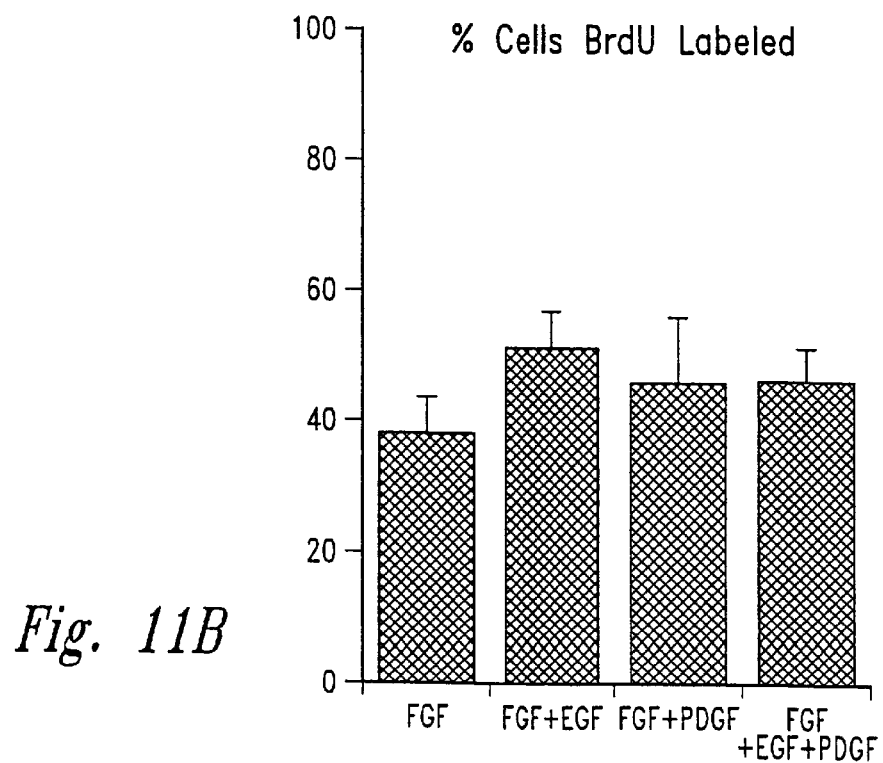
Figure 12A:
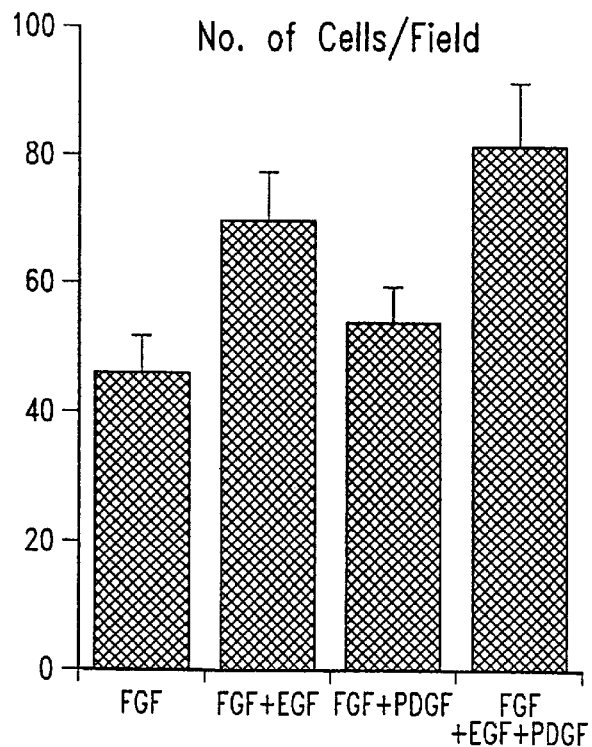
FIGS. 12A and 12B are histograms depicting the number of cells per field (FIG. 12A) and the percent of cells labeled by BrdU (FIG. 12B) for a representative human clonal CNS progenitor cell line (C10) following culture in the presence of FGF-2 (column 1), FGF-2 and EGF (column 2), FGF-2 and PDGF A/B (column 3) or FGF-2, EGF and PDGF A/B (column 4). In each case, the level of FGF-2 was 40 ng/mL. When added, the level of human recombinant EGF was 40 ng/mL and the level of human recombinant PDGF A/B was 20 ng/mL.
Figure 12B:
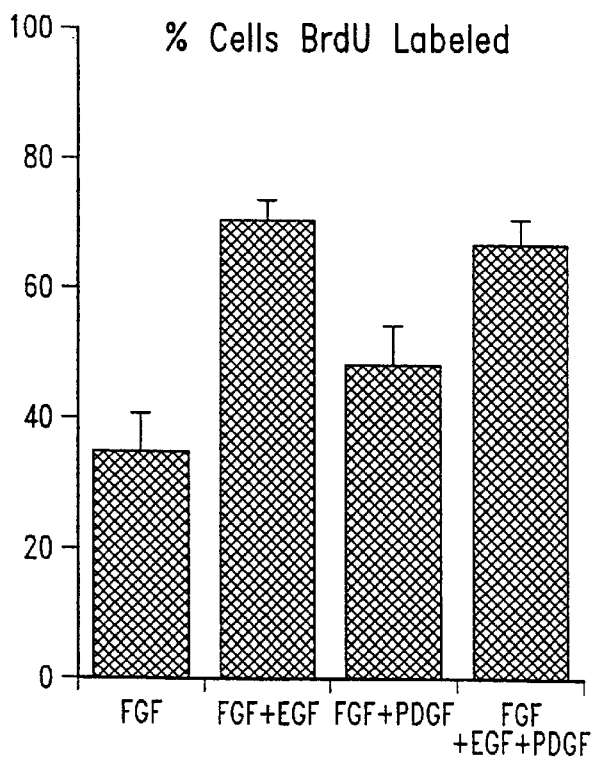

EGF and PDGF Enhance Proliferation Rate and Cell Survival. To facilitate the expansion of the human CNS clones, we identified factors that increase the proliferation rate and/or cell survival. To examine the effects of EGF and PDGF on the proliferation and survival of the human CNS clones, 40 ng/mL EGF, 20 ng/mL PDGF or both were added to the standard growth medium, which already contained FGF-2 and 50% CM, and total cell number and BrdU uptake and incorporation were assessed as described above. For clone C2, EGF or PDGF addition increased the total cell number (FIG. 11A) by approximately 2-fold. This increase in cell number was due to enhanced cell viability (decreased cell death), since there were only slight increases in proliferation rate (assessed by BrdU uptake and incorporation, FIG. 11B). The effects of EGF and PDGF were not additive, suggesting that they share a common mechanism of action. In the case of clone C10, EGF (but not PDGF) addition increased the total cell number (FIG. 12A) by approximately 40%. Addition of EGF and PDGF increased the total cell number slightly further. This increase in cell number was due, at least in part, to enhanced proliferation rates; BrdU uptake and incorporation increase about 2-fold with EGF or EGF+PDGF addition (FIG. 12B), and doubling times (based on cell counts as a function of days in vitro, data not shown) decreased from 3 days (no EGF or PDGF addition) to 2 days (EGF+PDGF addition). Taken together, these data show that survival and proliferation are enhanced by the inclusion of EGF and PDGF, in addition to FGF-2, in the growth medium. As a result, all three growth factors were subsequently included in the growth medium used for these as well as other clones.

Clonality of Cell Lines B4, C2, E5 and C10. Human conditionally-immortalized CNS progenitor cell lines B4, C2, E5 and C10 are distinct clones. Genomic Southerns were carried out to confirm the clonality of cell lines C2 and C10. As a control, DNA from the clonal adult rat hippocampal neuronal line HC2S2, immortalized with the same retroviral vector (Hoshimaru et al., *Proc. Natl. Acad. Sci. USA* 93:1518–1523, 1996), was examined in parallel. The bulk-immortalized cells were also examined to obtain an indication of the number of different clones present in the mixture.

Genomic DNA was prepared from about $10^7$ cells using standard methods. The DNA was digested with restriction enzymes that cut in the integrated provirus (BamHI (ProMega, Madison, Wis.); EcoRI (ProMega, Madison, Wis.); or HindIII (New England BioLabs (Beverly, Mass.)). The digested DNA was resolved on an 0.8% agarose gel, transferred to a nylon membrane, and hybridized to a $^{32}$P-labeled probe against the PstI-PstI fragment of v-myc (Lofstrand Labs Limited, Gaithersburg, MD).

Figure 13:
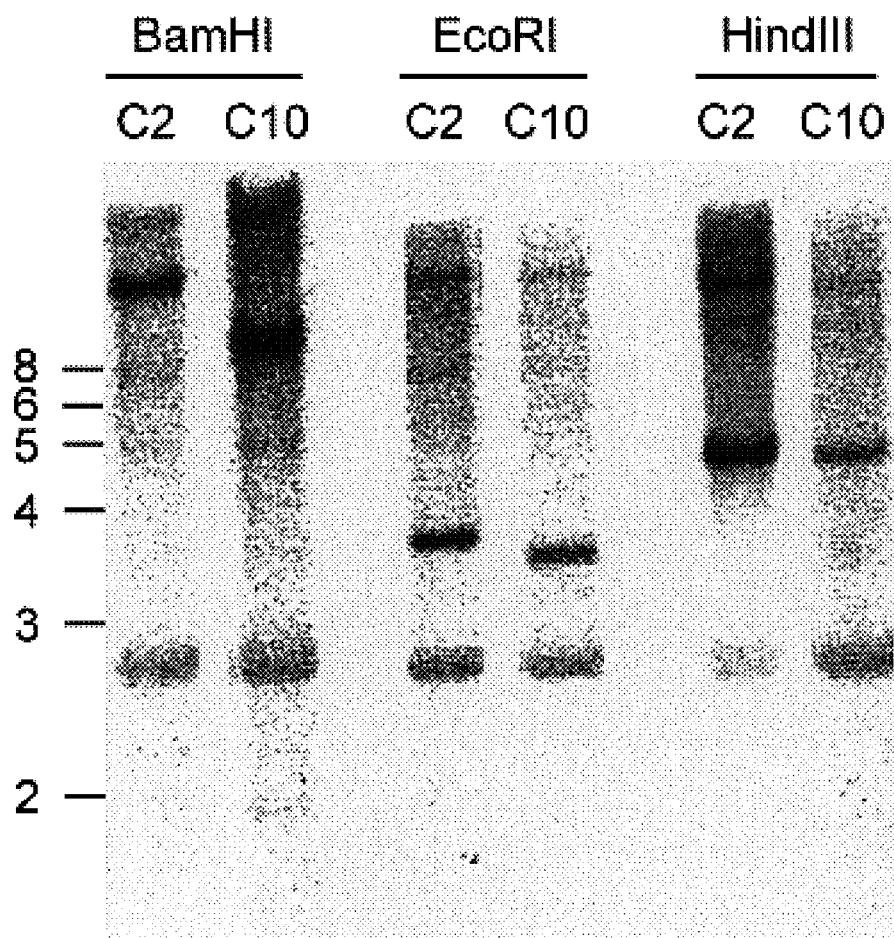
FIG. 13 is an autoradiogram showing the DNA fragment sizes that hybridize to a v-myc probe following enzyme restriction of genomic DNA prepared from the representative clonal cell lines C2 (lanes 1, 3 and 5) and C10 (lanes 2, 4 and 6). The DNA was digested with BamHI (lanes 1 and 2), EcoRI (lanes 3 and 4) or HindIII (lanes 5 and 6).

HindIII cuts within the LTR's produced unit length DNA fragments of 4.8 kb, as expected. Single bands (9 kb, 5.4 kb or 4.8 kb, respectively) resulted from each of the restriction digests of HC2S2 DNA with BamHI, EcoRI or HindIII, respectively. From clone C2, single bands of 11 kb, 3.6 kb and 4.8 kb resulted from BamHI, EcoRI or HindIII restriction digests, respectively (FIG. 13 and Table 2, below). From clone C10, single bands of 9 kb, 3.5 kb or 4.8 kb resulted from BamHI, EcoRI or HindIII restriction digests, respectively (FIG. 13, Table 2). Single bands of distinct sizes resulted from restriction digests of clones B4 (BamHI: 6.8; EcoRI: 3.7; HindIII: 4.8), JA3 (BamHI: 13; EcoRI: 6.0; HindIII: 4.8), JD4 (BamHI: 9.5; EcoRI: 3.6; HindIII: 4.8), JE8 (BamHI: 13; EcoRI: 7.0; HindIII: 4.8) and E5 (EcoRI: 4.6) (Table 2). The bulk-immortalized cells gave about 10 bands (3–11 kb) of equal intensity (data not shown) after restriction digest with either BamHI or EcoRI, suggesting that about 10 distinct clones were present in the mixture.

TABLE 2

Immortalized Human Fetal CNS Lines:
$^{32}$P-v-myc Labeled Fragment Sizes after DNA Restriction

| Cell Line | BamHI | EcoRI | HindIII |
|---|---|---|---|
| B4 | 6.8 kb | 3.7 kb | 4.8 kb |
| C2 | 11 kb | 3.6 kb | 4.8 kb |
| C10 | 9 kb | 3.5 kb | 4.8 kb |
| E5 | n.d. | 4.6 kb | n.d. |
| JA3 | 13 kb | 6.0 kb | 4.8 kb |
| JD4 | 9.5 kb | 3.6 kb | 4.8 kb |
| JE8 | 13 kb | 7.0 kb | 4.8 kb |

B. Characterization of Clonal Cell Lines

1. Characterization of Clone B4

Figure 14A:
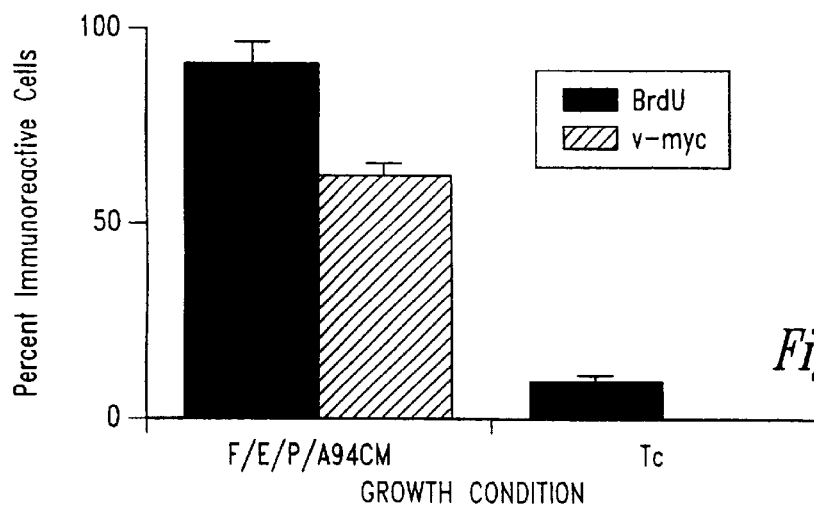
FIGS. 14A, 14B and 14C are histograms depicting the percent of cells within a representative conditionally-immortalized human clonal CNS cell line (B4) that are immunoreactive with probes for BrdU (FIG. 14A, solid bars), v-myc (FIG. 14A, hatched bars), MAP2a/b (FIG. 14B, solid bars), NF200kD (FIG. 14B, hatched bars), GFAP (FIG. 14C, solid bars) or GalC (FIG. 14C, hatched bars). In each case, the immunoreactivity was evaluated in proliferative conditions (growth medium containing FGF-2, EGF, PDGF A/B and conditioned medium) and in differentiation conditions (after growth in the presence of tetracycline, Tc, for 5 days).
Figure 14B:
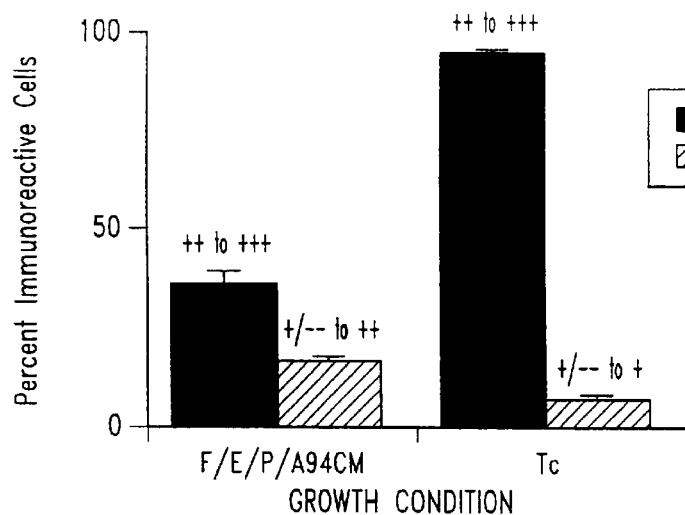
Figure 14C:
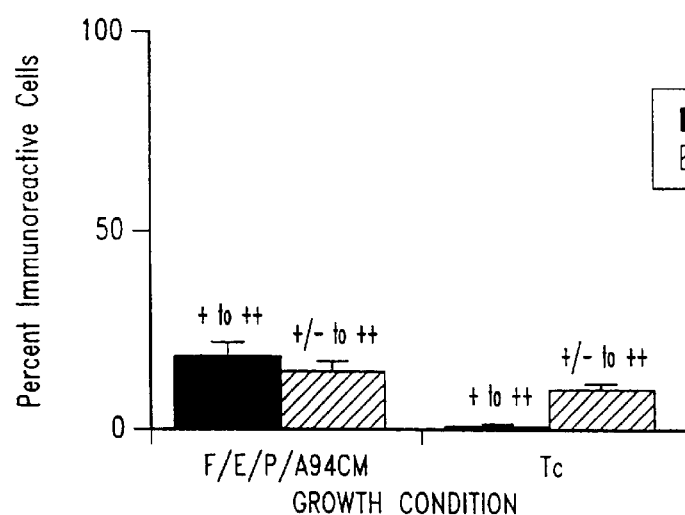
Figure 15:
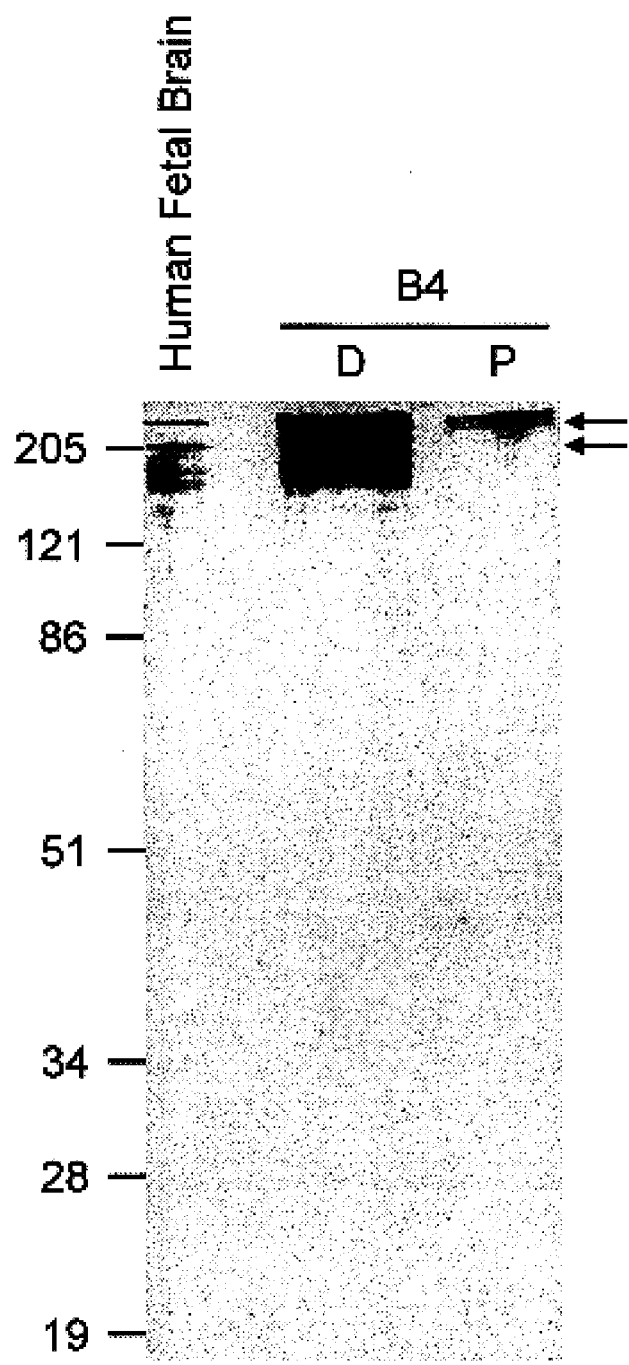
FIG. 15 is a Western blot of the level of MAP2a/b in human fetal brain tissue (lane 1), differentiated B4 cells (lane 2) or proliferating B4 cells (lane 3). Differentiated B4 cells were grown in medium containing tet and RA for 1 day, followed by growth in medium containing tet, high $K^+$, NT-3 and BDNF for 5 days.

Clone B4 is neuronally specified Clone B4 is relatively robust and grows rapidly in proliferative conditions. Immunoreactivity of the cells was evaluated as described above. In proliferative conditions, almost all cells stain for BrdU after overnight uptake and about 2/3 of the cells are immunoreactive for v-myc (nuclear labeling). Relatively few cells labeled for MAP2a/b, NF (200 kD), GFAP or GalC (FIG. 14). After differentiation with tetracycline alone for about 1 week, cells stopped proliferating, became phase-bright and extended long processes. Moreover, BrdU uptake and v-myc immunoreactivity were largely suppressed whereas MAP2a/b labeling was present in almost all cells. Western blot analysis confirmed the up-regulation of MAP2a/b upon differentiation of clone B4 (FIG. 15). These results, together with the absence of GFAP and GalC labeling, indicate that clone B4 differentiates into neurons upon suppression of the oncogene. However, NF (200 kD) and tau immunolabeling remained low, suggesting that these cells were not yet fully mature.

To promote further neuronal maturation the effects of additional differentiating agents on clone B4 were examined. Tau immunoreactivity remained low (<10% of cells) after 7–8 days of differentiation with tet, NT-3 and BDNF; tet, high $K^+$, NT-3 and BDNF; tet and RA for 1 day followed by tet, high $K^+$, NT-3 and BDNF; tet, NT-3 and GDNF; tet, high $K^+$, NT-3 and GDNF; tet and RA for 1 day followed by tet, high $K^+$, NT-3 and GDNF; tet and sonic hedgehog protein (shh); tet and RA for 5 days followed by tet and shh; tet, shh and high $K^+$; tet, shh and BDNF; tet, shh and GDNF, tet, shh, GDNF and high $K^+$; tet, shh, BDNF and GDNF; or tet, shh, BDNF, GDNF and high $K^+$. Based on morphology (Table 3) and immunocytochemical staining, growth with phorbol ester (PMA), human serum or rat serum prevented tet from inducing neuronal differentiation, whereas growth with forskolin promoted further neuronal differentiation and process outgrowth over tet alone, or tet+BDNF+NT-3+ GDNF. Moreover, PMA prevented the combination of tet, BDNF, NT-3, GDNF and forskolin from promoting neuronal differentiation.

TABLE 3

Human CNS Line B4: Effects of Growth Conditions (4d) on Neuronal Differentiation

| Growth Condition | Morphology |
| --- | --- |
| Tc | + |
| Tc (2d); Tc + HS | − |
| Tc (2d); Tc + RS | − |
| Tc + PMA | − |
| Tc + FSK | ++ |
| TcNBG | + |
| TcNBG + RA | + |
| TcNBG + PMA | − |
| TcNBG + FSK | ++ |
| TcNBG + RA + FSK | ++ |
| TcNBG + RA + PMA | − |
| TcNBG + PMA + FSK | − |
| TcNBG (2d); TcNBG + HS | − |
| TcNBG (2d); TcNBG + RS | − |

Figure 16:
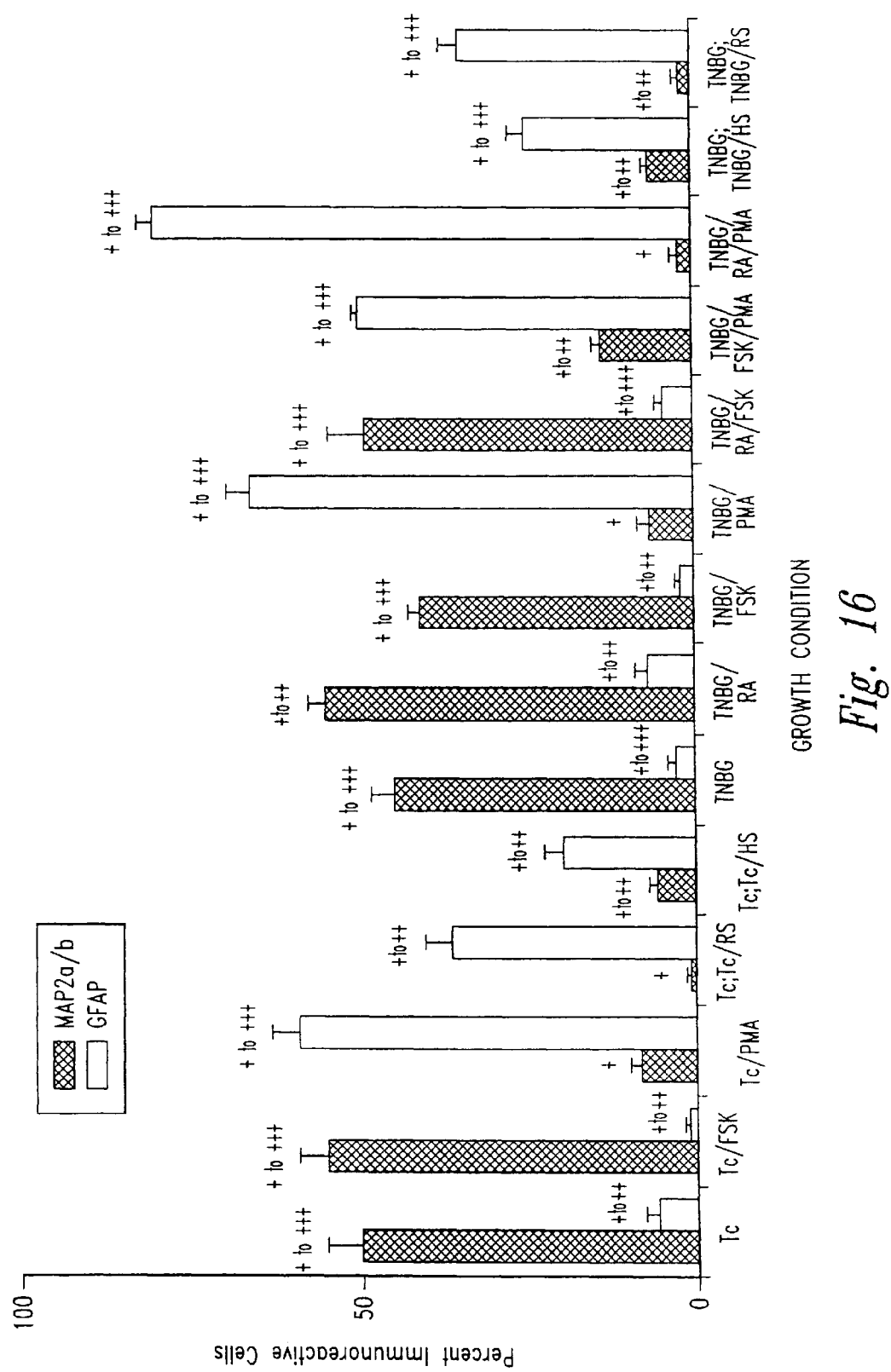
FIG. 16 is a histogram illustrating the percent of cells within a representative conditionally-immortalized human clonal CNS cell line (B4) that are immunoreactive with probes for MAP2a/b (dark bars) or GFAP (white bars) following differentiation under a variety of growth conditions. Cells were differentiated in the presence of tetracycline (Tc, columns 1–2); tetracycline and forskolin (Tc/FSK, columns 3–4); tetracycline and PMA (Tc/PMA, columns 5–6); tetracycline, followed by tetracycline and rat serum (Tc; TcRS, columns 7–8); tetracycline, followed by tetracycline and human serum (Tc; TcHS, columns 9–10); tetracycline, NT-3, BDNF and GDNF (TNBG, columns 11–12); tetracycline, NT-3, BDNF, GDNF and retinoic acid (TNBG/RA, columns 13–14); tetracycline, NT-3, BDNF, GDNF and forskolin (TNBG/FSK, columns 15–16); tetracycline, NT-3, BDNF, GDNF and PMA (TNBG/PMA, columns 17–18); tetracycline, NT-3, BDNF, GDNF, retinoic acid and forskolin (TNBG/RA/FSK, columns 19–20); tetracycline, NT-3, BDNF, GDNF, forskolin and PMA (TNBG/FSK/PMA, columns 21–22); tetracycline,.NT-3, BDNF, GDNF, retinoic acid and PMA (TNBG/RA/PMA, columns 23–24); tetracycline, NT-3, BDNF and GDNF, followed by tetracycline, NT-3, BDNF, GDNF and human serum (TNBG; TNBG/HS, columns 25–26); tetracycline, NT-3, BDNF and GDNF, followed by tetracycline, NT-3, BDNF, GDNF and rat serum (TNBG; TNBG/RS, columns 27–28).
Figure 17:
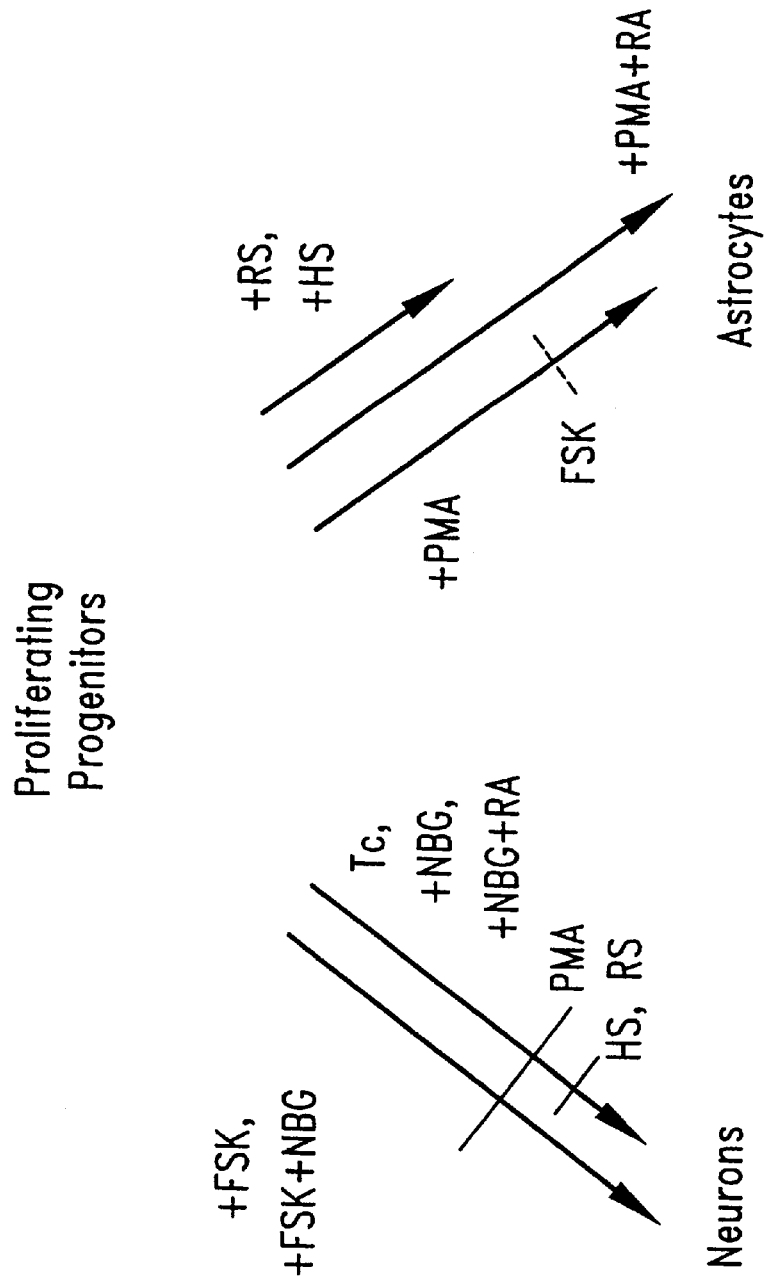
FIG. 17 is a diagram illustrating a model for human CNS lineage.

HS (human serum), 5%; RS (rat serum), 5%; PMA, 20 nM; FSK, 10 $\mu$M; RA, 0.5 $\mu$M; NT-3 (N), 20 ng/mL; BDNF (B), 20 ng/mL; GDNF (G), 20 ng/mL To examine the effect of growth conditions on cell lineage, clone B4 was examined for MAP2a/b and GFAP immunoreactivities (FIG. 16) after growth with serum, PMA, forskolin and/or retinoic acid. Although clone B4 is a specified neural precursor (i.e., after suppressing the oncogene with tet, only neuronal differentiation occurs), some growth conditions could override this predilection and promote astrocytic differentiation. PMA strongly promoted astrocytic differentiation and overrode the effects of forskolin when both agents were added together. Retinoic acid was a general differentiation agent, enhancing the effects of the other agents (PMA or forskolin) present in the growth medium. These data support the model for human CNS cell lineage depicted in FIG. 17.

Figure 18:
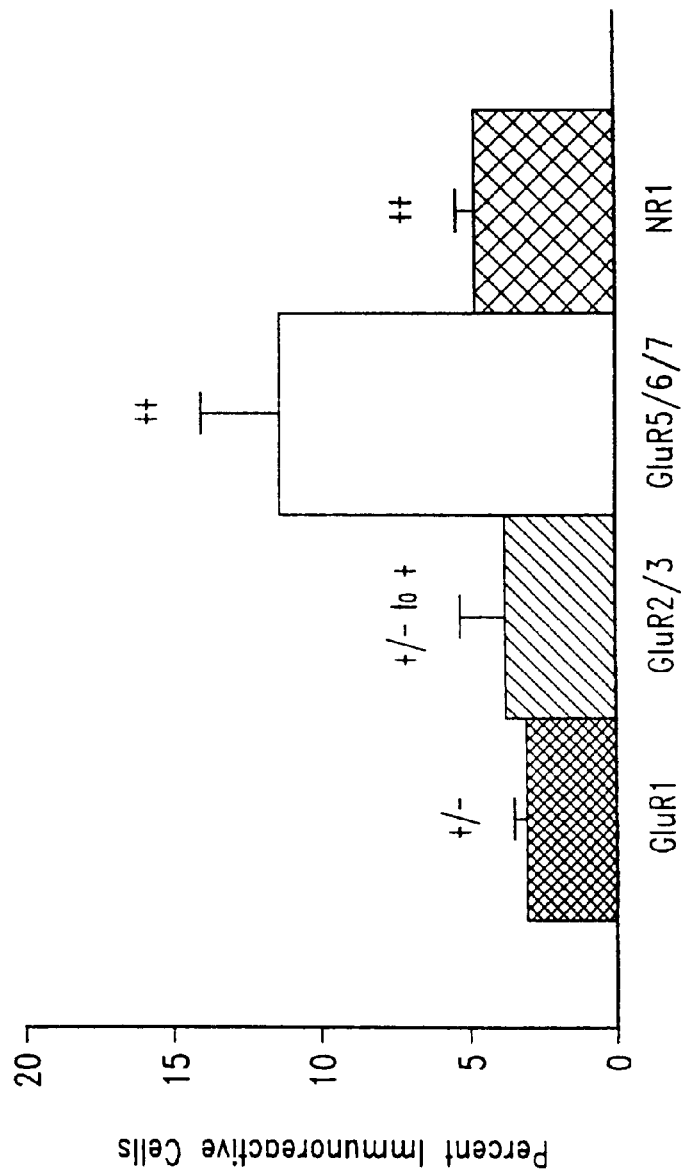
FIG. 18 is a histogram illustrating the levels of glutamate receptor subunits in a representative differentiated human clonal CNS progenitor cell line (B4). The levels are presented as percent immunoreactive cells, and the subunits assayed were GluR1 (column 1), GluR2/3 (column 2), GluR5/6/7 (column 3) and NR1 (column 4).

Clone B4 contains GluR1-5 (PCR and immunocytochemistry) and NR1 (immunocytochemistry). Immunoreactivity of B4 cells for glutamate receptor subunits was evaluated as described above. A sub-population of cells exhibited immunoreactivity for the glutamate receptor subunits after differentiation by growth with tet+RA+NT-3+BDNF for 23 days (FIG. 18). The NMDA receptor subunit NR1 is required for functional receptors; ~5% of differentiated B4 cells were strongly immunoreactive for this subunit.

The levels of mRNA encoding glutamate receptor subunits were also evaluated for clone B4 via PCR. For proliferating conditions, clone B4 at passage 15 or 24 was grown with FGF-2, EGF, PDGF and conditioned medium, as described above, for 3 days. Differentiation was achieved by growth of clone B4 (again at passage 15 or 24) for 8 days in tetracycline, high $K^+$, NT-3 and BDNF, as described above. Human fetal brain tissue (200 mg) or cell pellets (~0.5 to $4\times10^6$ cells) were snap-frozen and stored at −80° C. until mRNA isolation. PolyA$^+$ RNA was prepared using the Micro-FastTrack Kit (Invitrogen, San Diego, Calif.). 0.5 to 2.0 ng of this mRNA template was then reverse transcribed to generate full-length first-strand cDNA using the Ready To Go T-Primed First Strand Kit (Pharmacia Biotech, Piscataway, N.J.). PCR primers were designed using human sequences obtained from the GenBank database, and Oligo software. For PCR amplification, 15 ng of cDNA template was incubated with the oligonucleotide pair and 2.5 units of Taq polymerase (Perkin-Elmer, Foster City, Calif.) in 100 $\mu$L of assay buffer containing 100 mM Tris-HCl, pH 8.3; 500 mM KCl. Cycle parameters were: 5 min at 94° C., 5 min at 55° C., 1 min at 72° C., 1 min at 94° C. 1 min at 55° C., followed by 7 min at 72° C. for 35 cycles. The resultant products were resolved on 1.2% agarose gels and stained with ethidium bromide for visualization. PCR conditions were optimized using human fetal brain cDNA as a positive control and cDNA libraries from Hela (GluR1-7), CHO (adenosine $A_2$, mGlu5b and 5-HT1A), 3T3 (5-HT2a) or HEK293 (GABAR $\alpha$1) cells as negative controls. If a prominent band of the correct size was present in the positive control, then the following additional controls were carried out to verify that the PCR product was gene-specific: reverse transcriptase omission during cDNA preparation, RNase addition during mRNA preparation, PCR with each primer alone, and sequence-specific probe hybridization. Primer sets used were:

NMDAR1 5' primer: 5'-AACCTGCAGAACCGCAAG-3' (1063–1080) (SEQ ID NO:1)
   3' primer: 5'-GCTTGATGAGCAGGTCTATGC-3' (1376–1396) (SEQ ID NO:2)

GluR1 5' primer: 5'-AGATTTGCTTTGTGGCAA-3' (230–247) (SEQ ID NO:3)
   3' primer: 5'-ATTCTCCAGGTCCTGAAA-3' (668–685) (SEQ ID NO:4)

GluR2 5' primer: 5'-CGGAAGATTGGCTACTGG-3' (1310–1327) (SEQ ID NO:5)
   3' primer: 5'-TTAGCCGTGTAGGAGGAG-3' (2062–2080) (SEQ ID NO:6)

GluR3 5' primer: 5'-GACACACGACGCAATACTGG-3' (980–999) (SEQ ID NO:7)
   3' primer: 5'-TGAGAATACGCCTGGTTTTG-3' (1672–1691) (SEQ ID NO:8)

GluR4 5' primer: 5'-TGGTACGAGAGGAGGTCATT-3' (1514–1534) (SEQ ID NO:9)
   3' primer: 5'-TCTGGCTTTGTTTCTTATGG-3' (2561–2580) (SEQ ID NO:10)

GluR5 5' primer: 5'-CAAAGACAAGTCCAGCAA-3' (1254–1271) (SEQ ID NO:11)

3' primer 5'-CCAACTCCAAACCAGAAA-3' (183A-1850) (SEQ ID NO:12)

GluR6 5' primer: 5'-TTTGCTGGATGGATTTATG-3' (930–949) (SEQ ID NO:13)

3' primer: 5'-AAAGAACGATTGGATAAGG-3' (1280–1298) (SEQ ID NO:14)

GluR7 5' primer: 5'-GCGTCTTCTCCTTCCTCAATC-3' (1676–16964) (SEQ ID NO:15)

3' primer: 5'-ATGCCCTCCTCGTTGTTCTTC-3' (2175–2195) (SEQ ID NO:16)

Figure 19:
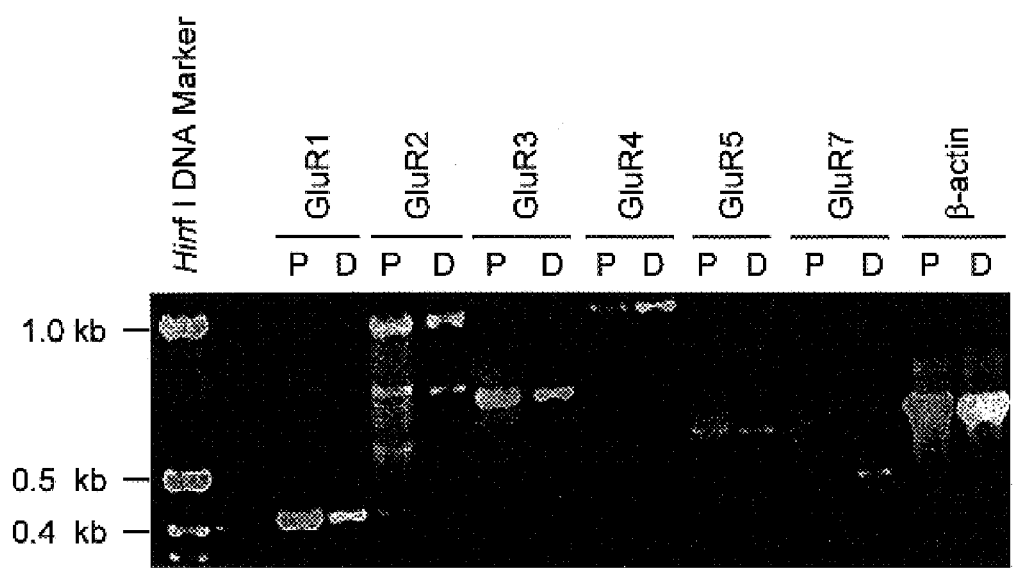
FIG. 19 is a photograph illustrating the PCR analysis of a representative differentiated human clonal CNS progenitor cell line (B4) for glutamate receptor subunit mRNA. PCR was performed using primers specific for GluR1 (lanes 2 and 3), GluR2 (lanes 4 and 5), GluR3 (lanes 6 and 7), GluR4 (lanes 8 and 9), GluR5 (lanes 10 and 11), GluR7 (lanes 12 and 13) and β-actin as a control (lanes 14 and 15). In each case, even numbered lanes represent analysis after growth in proliferating conditions and odd numbered lanes represent analysis after differentiation. HinfI DNA markers are shown in lane 1.

The results are presented in FIG. 19. The expected PCR product sizes are GluR1 (409 bp), GluR2 (770 bp), GluR3 (712 bp). GluR4 (1,067 bp), GluR5 (597 bp), GluR7 (520 bp). Clone B4 was positive for GluR1, GluR2, GluR3, GluR4 and GluR5. Clone B4 was negative for GluR7 under proliferating conditions and positive under differentiating conditions. The presence of mRNA for GluR1–4 and immunoreactivity (although weak) for GluR1 and GluR2/3 (FIG. 18) suggested that clone B4 expresses the AMPA-preferring subtype of glutamate receptor, whereas the presence of mRNA for GluR5 and GluR7 and immunoreactivity for GluR5/6/7 suggested that these cells express the low-affinity kainate receptor.

Clone B4 contains GABA, 5-HT and Adenosine subunits (PCR). PCR analyses performed as described above demonstrated that clone B4 expressed mRNA for GABAR$\alpha$5, 5-HT1D$\beta$, 5-HT1E, 5-HT2A, 5-HT2B, 5-HT7, and adenosine A1 and A2B receptor subunits (data not shown). These subunits are normally coupled to changes in cAMP levels, IP3/DG and ion channel activity. Thus, this cell line enables studies of potentially functional receptors in their native environment, with normal intracellular signaling pathways and coupling mechanisms.

Figure 20:
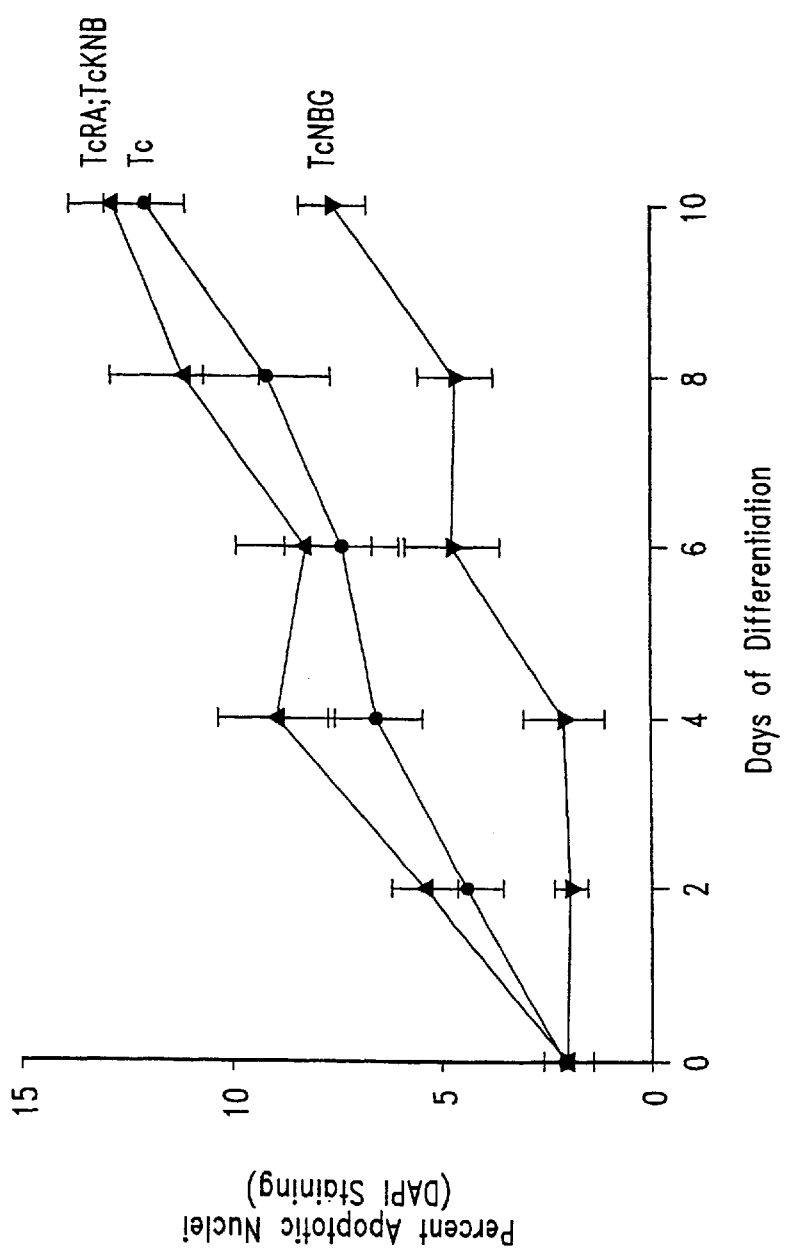
FIG. 20 is a graph showing the time course of basal apoptosis during differentiation of a representative human clonal CNS progenitor cell line (B4). The percentage of apoptotic nuclei was determined by DAPI staining after 0 to 10 days of differentiation in tetracycline alone (Tc); tetracycline, NT-3, BDNF and GDNF (TcNBG); or tetracycline and retinoic acid for 1 day, followed by tetracycline, high $K^+$, NT-3 and BDNF (TcRA;TcKNB) as indicated.

Clone B4 undergoes apoptosis in 2 models of cell death. A robust assay for apoptosis requires a substantial increase in the index of apoptosis over baseline levels of apoptosis. After differentiation with tet alone, clone B4 exhibited significant levels of basal apoptosis. In order to minimize this basal level of apoptosis, sister cultures were differentiated in several types of growth media, and the percentages of apoptotic nuclei were determined by DAPI staining after 0 to 10 days of differentiation (FIG. 20). Cultures differentiated with tet+NT-3+BDNF+GDNF exhibited the lowest levels of apoptosis during this time period. Sister cultures differentiated with tet alone, or tet+retinoic acid for 1 day, followed by tet+high K$^+$+NT-3 +BDNF, had 2 to 3-fold higher levels of apoptosis. Moreover, since the percentage of apoptotic nuclei generally increased during the first 10 days of differentiation, the best window of time for using the cells in apoptosis assays was between 5 and 7 days of differentiation. At this time, <5% of cells were apoptotic, yet sufficient neuronal differentiation of the overall population of cells had occurred.

Figure 21A:
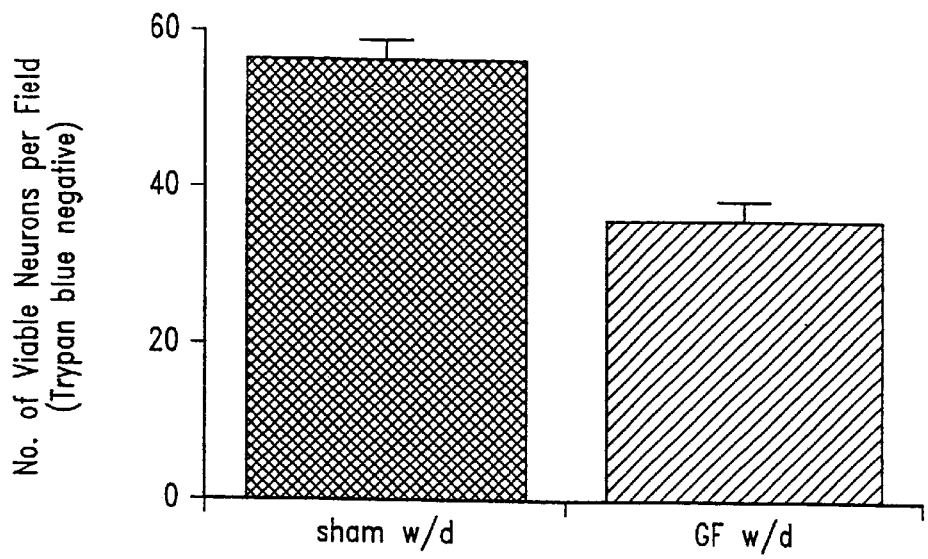
FIGS. 21A and 21B are histograms showing the effect of growth factor withdrawal on the number of viable neurons (Trypan blue negative, FIG. 21A) and the percent of apoptotic nuclei (DAPI staining, FIG. 21B) within a representative differentiated clonal human CNS progenitor cell line (B4). In each case, the first column represents the value obtained in the presence of growth factors, and the second shows the value following 48 hours (FIG. 21A) or 18 hours (FIG. 2) B) of growth factor withdrawal. B4 cells were differentiated by growth with tet, NT-3, BDNF and GDNF for 6–7 days.
Figure 21B:
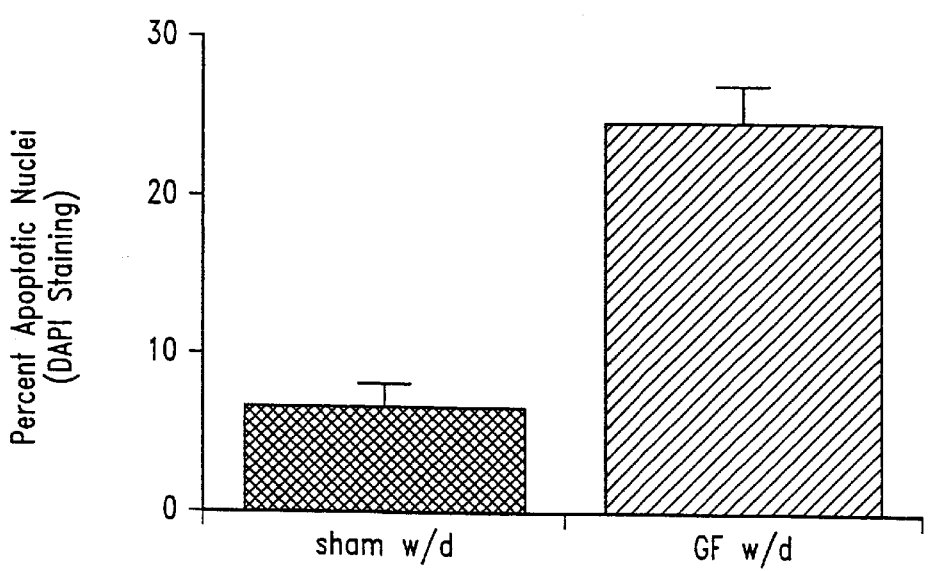

Withdrawal of growth factors and N2 supplement induces apoptosis in differentiated clone B4. After 48 hours of withdrawal of growth factors and N2 supplement, about 40% of neurons were no longer viable, as assessed by Trypan blue exclusion (FIG. 21). In 5 out of 6 experiments, there was an approximately 2-fold increase in the percentage of apoptotic cells with condensed nuclei after withdrawal of growth factors and N2 supplement for about 1 day (FIG. 21). These experiments, taken together with the presence of DNA laddering after withdrawal (data not shown), establish that withdrawal of growth factors and N2 supplement from differentiated clone B4 represents one model of apoptosis.

Figure 22:
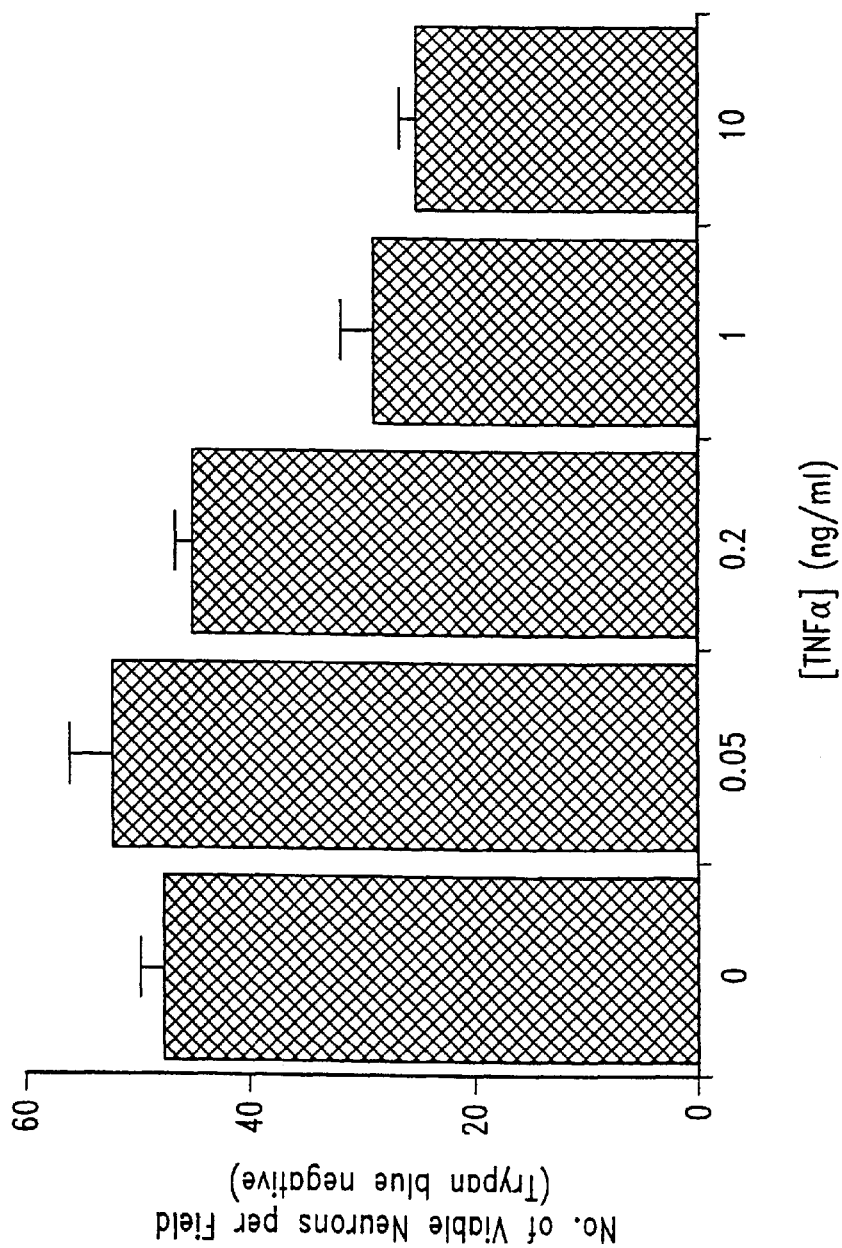
FIG. 22 is a histogram showing the number of viable neurons per field (assessed by Trypan blue exclusion) 48 hours after the addition of TNFα (0, 0.05, 0.2, 1 or 10 ng/mL, as indicated) to a representative differentiated clonal human CNS progenitor cell line (B4). B4 cells were differentiated by growth with tet+RA for 1 day, followed by tet, high $K^+$, NT-3 and BDNF for 6 days.
Figure 23:
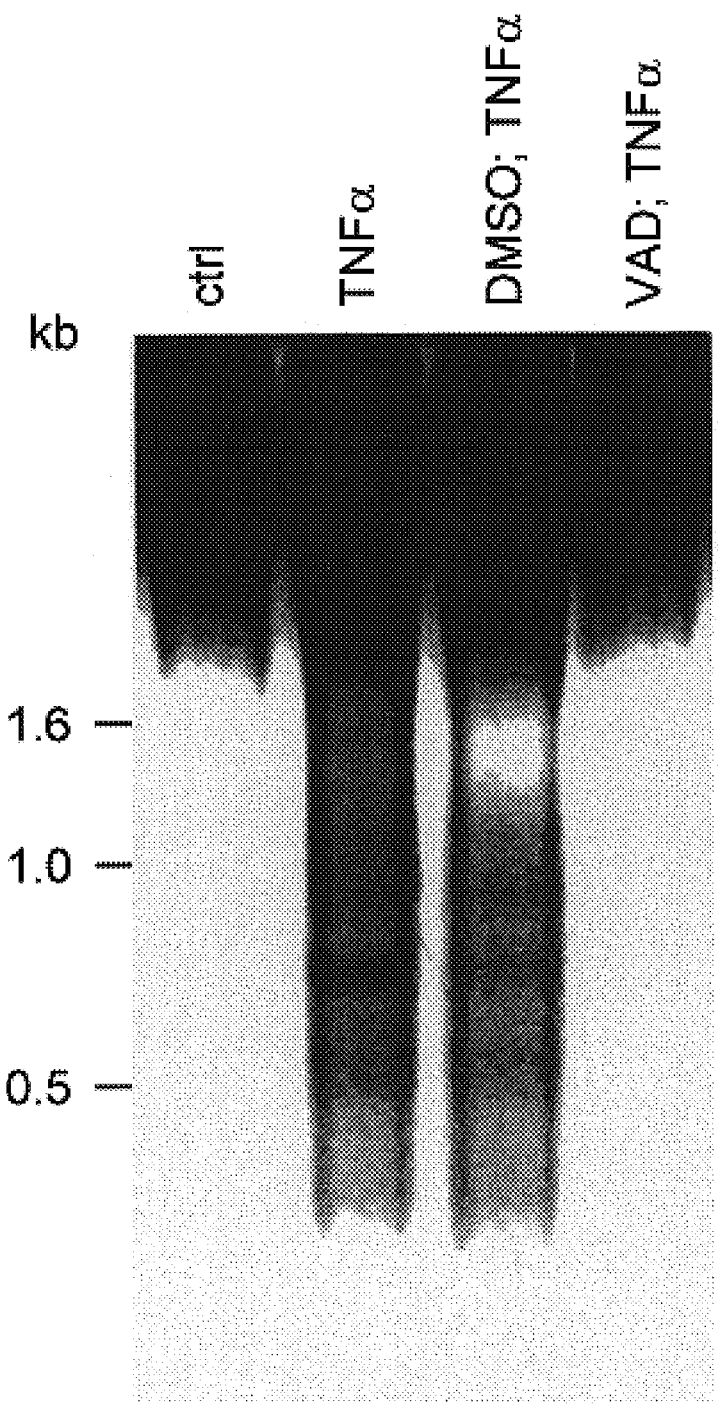
FIG. 23 is a photograph illustrating the extent of DNA laddering in DNA prepared from representative differentiated human CNS progenitor cells (clone B4) and analyzed by gel electrophoresis. Lane 1 shows the control DNA, lane 2 shows DNA prepared from cells treated with TNFα (10 ng/mL), lane 3 shows DNA prepared from cells treated with TNFα and DMSO and lane 4 shows DNA from cells treated with TNFα and the peptide aldehyde inhibitor Z-VAD (Z-Val-Ala-Asp-$Ch_2$F) at 80 μM.
Figure 24:
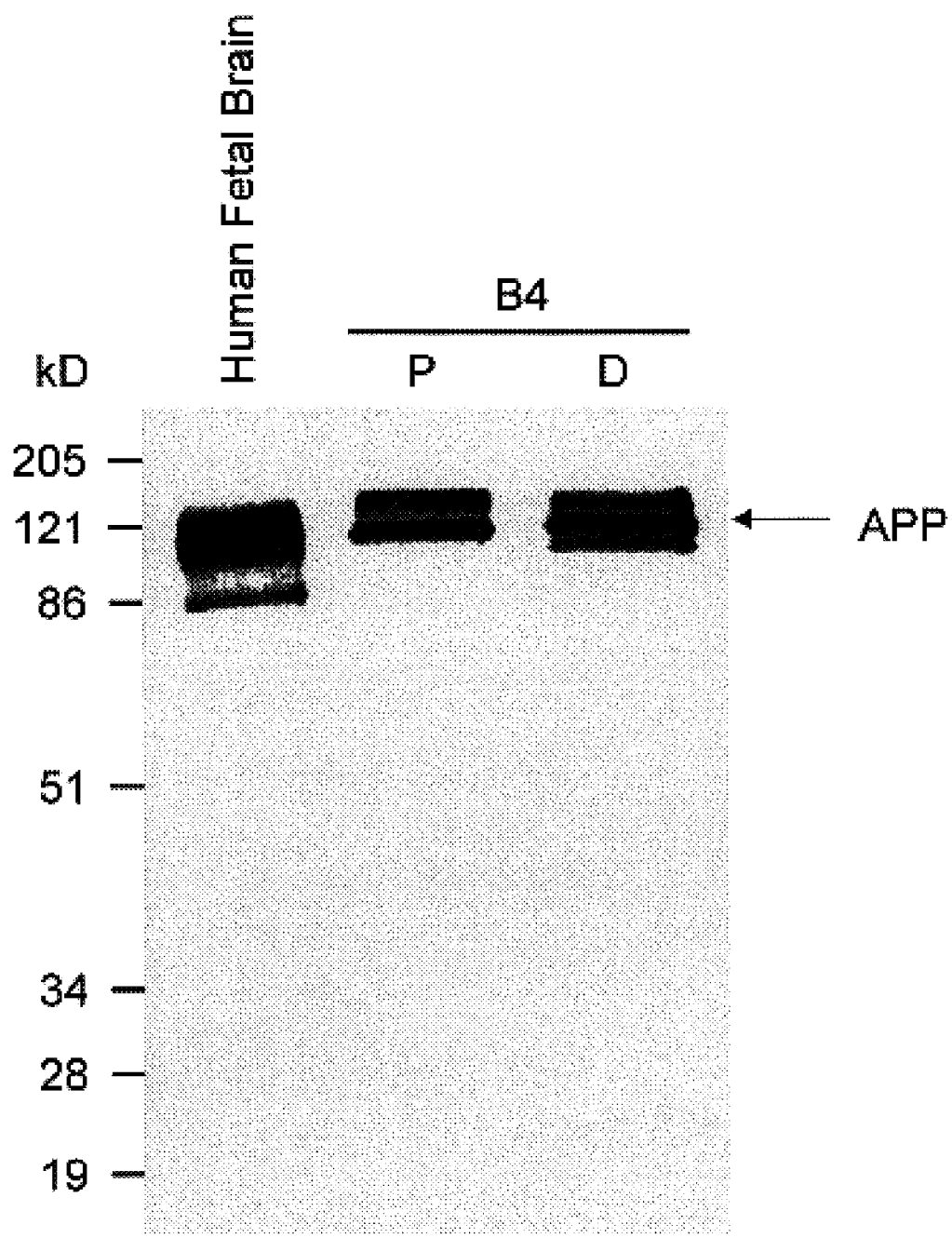
FIG. 24 is a Western blot showing the level of amyloid precurser protein (APP) expression in human fetal brain (lane 1), and in a representative clonal human CNS progenitor cell line (B4) after growth in proliferating conditions (lane 2) or in differentiating conditions (lane 3). The position of size markers is shown on the left, and the location of APP is indicated by the arrow on the right.

TNF$\alpha$ induces apoptosis in differentiated clone B4. After addition of TNF$\alpha$ (1 or 10 ng/mL), about 50% of neurons were no longer viable (assessed by Trypan blue exclusion, FIG. 22). Lower concentrations of TNF$\alpha$ (0.05 or 0.2 ng/mL) had little effect on neuronal viability. The effect of TNF$\alpha$ (10 ng/mL) was most pronounced after at least 48 hrs of treatment. Corresponding to the decline in viability, the percentage of apoptotic nuclei increased after treatment with TNF$\alpha$ (10 ng/mL, data not shown), and TNF$\alpha$ treatment also resulted in increased DNA laddering upon gel analysis (FIG. 23). Moreover, treatment with the peptide aldehyde inhibitor Z-VAD (Z-Val-Ala-Asp-Ch$_2$F) at 80 $\mu$M blocked the increase in DNA laddering (FIG. 23). These results indicate that TNF$\alpha$ treatment of differentiated clone B4 represents another model of apoptosis.

Clone B4 can be transiently transfected A number of transfection methods, including transient transfection with lipofectin, lipofectamine, cellfectin and Pfx1–8 have been tested for optimizing the transfection of $\beta$-actin/luciferase into proliferating tet/myc immortalized human CNS cells. To date, Pfx-2 appears to be the most efficient reagent. Transfection of $\beta$-gal, followed by histochemical staining, showed that about 2% of cells were transfected in the presence of Pfx-2. The ability to transfect clone B4 makes this cell line useful for experiments such as expression of cloned receptors in a neuronal environment and of constituitively expressed or dominant negative forms of kinases that may play a role in apoptosis.

Clone B4 expresses c-jun, JNK, MEK6, APP, S182, STM2, CPP32 and ICH-1$_L$ Western blot analyses have been carried out on the neuronal cell line, B4, for c-jun, MEK6, APP (FIG. 21), CPP32 and ICH-1$_L$. Substantial amounts of c-jun and MEK6 are present in clone B4 after growth in proliferative conditions; after differentiation, levels of c-jun are no longer detectable, whereas levels of MEK6 increase. JNK activity is also present in clone B4, and levels of activity increase after differentiation. Significant amounts of APP, CPP32 and ICH-1$_L$ are present in both proliferating and differentiated B4 cells. The presence of APP indicates that clone B4 could be used to study APP processing which is of particular interest in human neurons, whereas the presence of CPP32 and ICH-1$_L$ allow the role of these proteins in apoptosis of human neurons to be examined.

2. Characterization of Clone C2

Figure 25A:
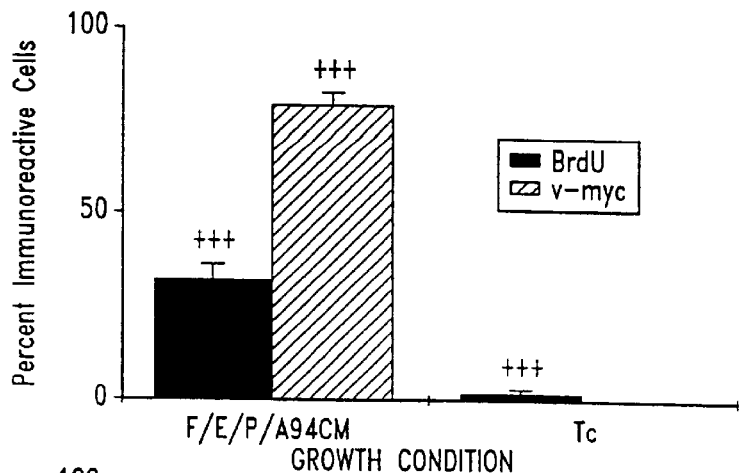
FIGS. 25A, 25B and 25C are histograms depicting the percent of cells within a representative human clonal CNS progenitor cell line (C2) that are immunoreactive with probes for BrdU (FIG. 25A, solid bars), v-myc (FIG. 25A, hatched bars), MAP2a/b (FIG. 25B, solid bars), NF200kD (FIG. 25B, hatched bars), GFAP (FIG. 25C, solid bars) or GalC (FIG. 25C, hatched bars). In each case, the immunoreactivity was evaluated in cells grown in proliferative conditions (growth medium containing FGF-2, EGF, PDGF and conditioned medium, columns 1–2) and in differentiation conditions (in the presence of tetracycline, Tc, for one week, columns 3–4).
Figure 25B:
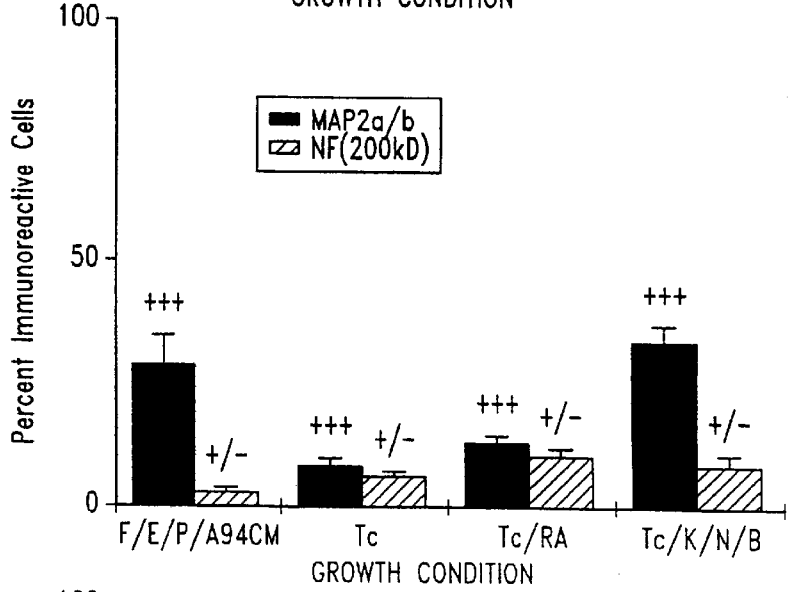
Figure 25C:
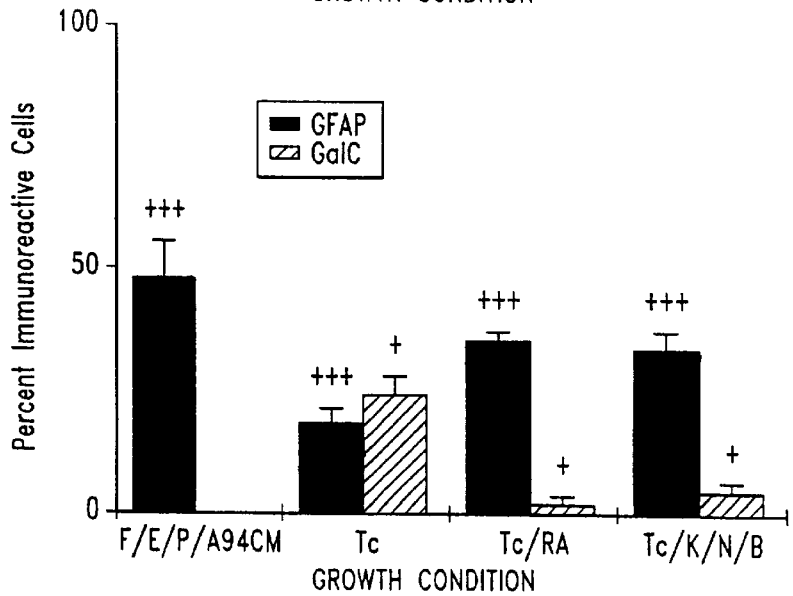

Clone C2 is multi-potent. In proliferative conditions, BrdU was taken up and v-myc was expressed in a substantial number of cells, whereas after growth in tet alone for 1 week, virtually no cells took up BrdU or expressed v-myc (FIG. 25A). About 30% of cells were MAP 2a/b-immunoreactive and about 30% were GFAP-positive (FIGS. 25B–C) in the proliferative condition. After differentiation with Tc, Tc/0.5 $\mu$M RA or Tc/20 mM K$^+$/NT-3/BDNF, the proportion of cells that expressed these cell-type specific markers did not change substantially. Thus, this clone is multi-potent and, although proliferation and myc expression are suppressed by tet, the expression of cell-type markers changes minimally upon differentiation.

Neurotransmitter receptor mRNA expression by clone C2 does not increase after differentiation with Tc/20 MM K/NT-3/BDNF. PCR for neurotransmitter receptor subunit mRNA indicated that receptor messages were not increased after differentiation. This is consistent with the immunocytochemical data which indicated that expression of cell-type specific markers in this clone does not respond substantially to differentiating conditions. Clone C2 (passage 9) was examined for the presence of mRNA for receptor subunits after growth with FGF-2. Bands of the correct size were present for GluR1, GluR2, GluR3, 5-HT1A, 5-HT2A and adenosine A$_2$ but not GluR4, GluR5, GluR7 or mGlu5b.

3. Characterization of Clone C10

Figure 26A:
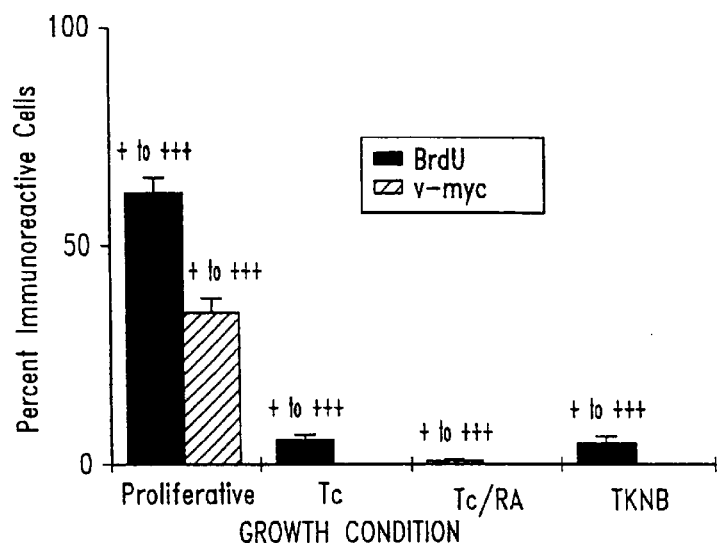
FIGS. 26A, 26B and 26C are histograms depicting the percent of cells within a representative conditionally-immortalized human clonal CNS cell line (C10) that are immunoreactive with probes for BrdU (FIG. 26A, solid bars), v-myc (FIG. 26A, hatched bars), MAP2a/b (FIG. 26B, solid bars), GFAP (FIG. 26B, hatched bars), GalC (FIG. 26C, solid bars) or fibronectin (FN).
Figure 26B:
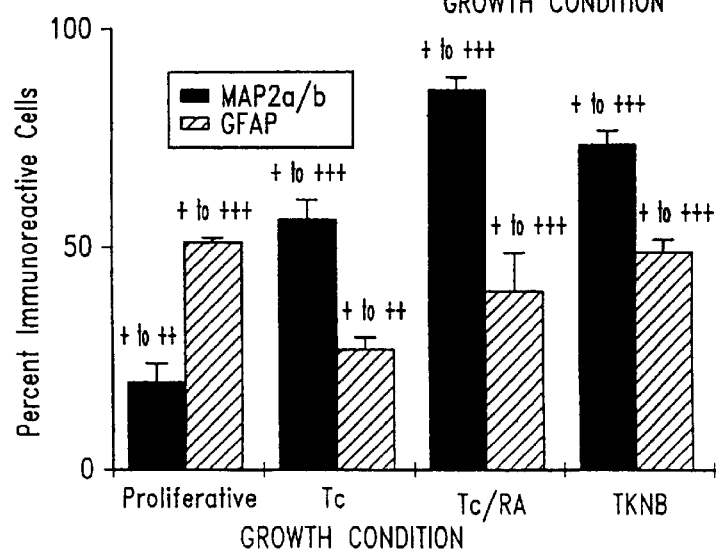
Figure 26C:
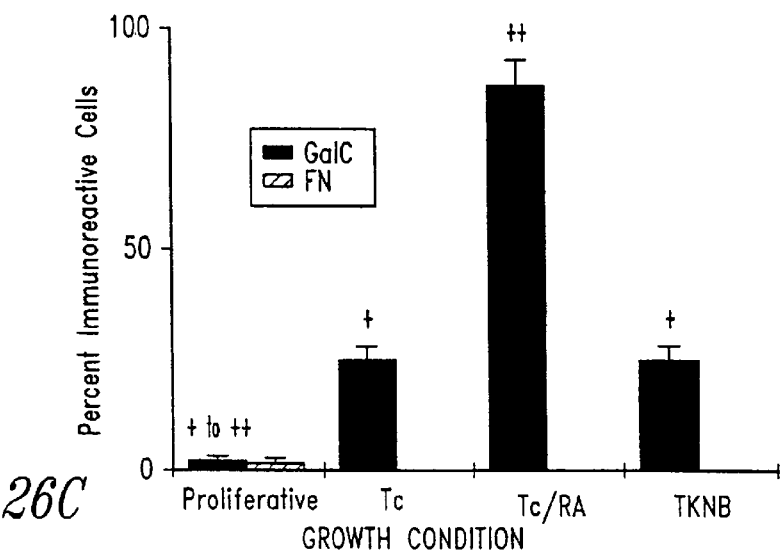

Clone C10 is multi-potent. In proliferative conditions:, BrdU and v-myc labeling was present in a substantial number of cells, whereas 19%, 51% or 0% of cells were MAP2a/b-, GFAP- or GalC-positive, respectively (FIGS. 26 A–C). After differentiation, the proportion of cells that expressed neuronal and oligodendrocyte markers increased significantly, with growth in tet+RA resulting in the highest proportions of cells expressing MAP2a/b or GalC. GFAP staining did not change after growth with tet+RA or tet+high $K^+$+BDNF+NT-3 whereas GFAP labeling decreased after growth in tet alone. These results indicate that this clone is multi-potent.

4. Characterization of Clone E5

Figure 27A:
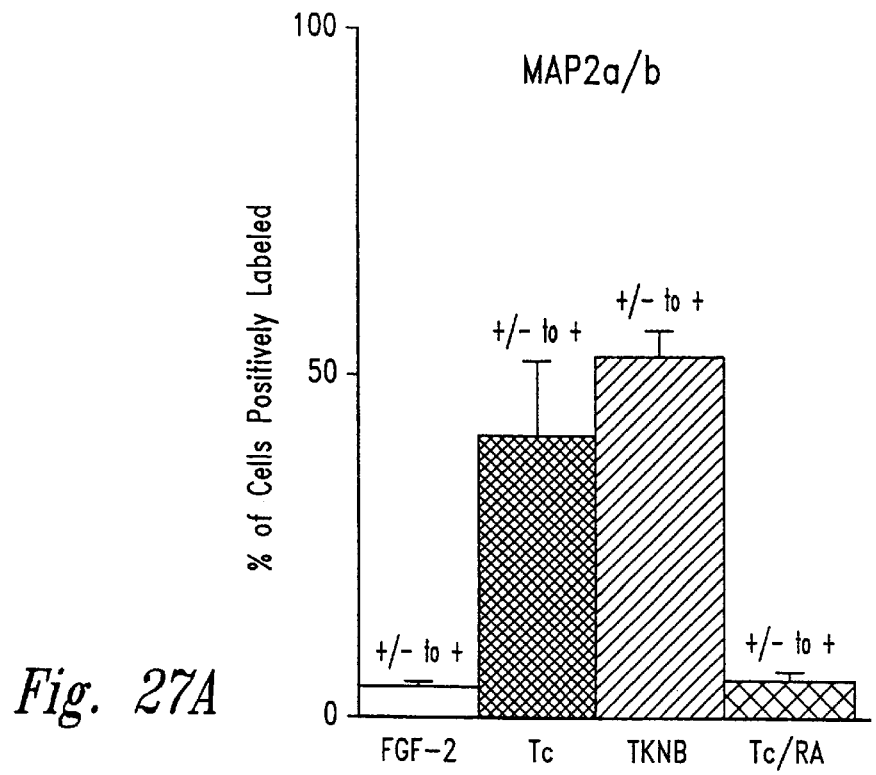
FIGS. 27A and 27B are histograms depicting the percent of cells within a representative human clonal CNS cell line (E5) that are immunoreactive with probes for MAP2a/b (FIG. 27A) and GFAP (FIG. 27B). In each case, the immunoreactivity was evaluated in cells grown in proliferative conditions (growth medium containing FGF-2, column 1); in the presence of tetracycline for one week (Tc, column 2); in cells grown in tetracycline, high K+, NT-3 and BDNF for one week (TKNB, column 3) and in tetracycline and RA for one week (Tc/RA, column 4).
Figure 27B:
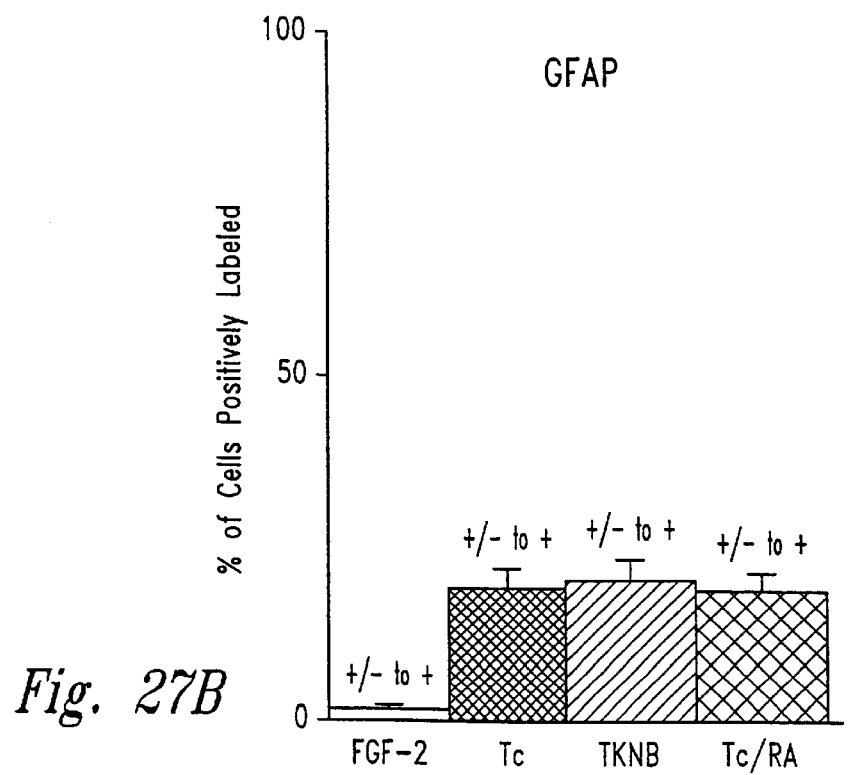

Clone E5 is an immature multi-potent cell. Clone E5 is multi-potential and likely represents an immortalized stem cell. In the proliferative growth condition (FGF-2), cells were polygonal and flat, doubled every 2 days, and exhibited virtually no labeling for the neuronal marker, MAP2a/b, or the astrocyte marker, GFAP (FIGS. 27A–B). After differentiation with tet, tet+high $K^+$+BDNF+NT-3, or tet+retinoic acid, there was no substantial change in morphology. After growth in tet or tet+high $K^+$+BDNF+NT-3, about 50% of cells stained to a small degree.for MAP2a/b, while about 20% stained to a small degree for GFAP. In contrast, after growth with tet+retinoic acid, virtually no cells stain for MAP2a/b, whereas staining for GFAP increased to 30%. These results suggest that clone E5 represents a multi-potent, immature stem cell.

From the foregoing, it will be appreciated that, although specific embodiments of the invention have been described herein for the purpose of illustration, various modifications may be made without deviating from the spirit and scope of the invention.

What is claimed is:

1. A method for producing a conditionally-immortalized human CNS cell, comprising:
   (a) plating human CNS progenitor cells on a surface that permits proliferation, said surface being tissue culture plastic or a surface treated with fibronectin;
   (b) adding serum-free growth medium to the cells;
   (c) allowing the CNS progenitor cells to proliferate in the serum-free medium;
   (d) transfecting the cells with DNA encoding a selectable marker and regulatable growth-promoting gene, wherein the growth-promoting gene encodes a protein selected from the group consisting of SV40 large T antigen, v-myc, N-myc, c-myc, p53, polyoma large T antigen, E1a adenovirus and E7 protein of human papilloma virus;
   (e) passaging the transfected cells onto a substrate; and
   (f) adding serum-free growth medium containing one or more proliferation-enhancing factors to the transfected cells, wherein said proliferation-enhancing factors are selected from the group consisting of FGF-2, PDGF, EGF, medium conditioned by perpetualized adult rat hippocampal progenitor cells, and a combination thereof;
   and therefrom producing a conditionally-immortalized human CNS progenitor cell that differentiates only upon suppression of the growth-promoting protein.

2. A conditionally-immortalized clonal human CNS progenitor cell that is transfected with an externally-regulated gene encoding a growth-promoting protein, wherein said cell differentiates into neurons and astrocytes, but not into oligodendrocytes, following suppression of production or growth-promoting activity of the growth-promoting protein.

3. A method for producing astrocytes and/or neurons, comprising culturing a cell produced according to claim 1 under conditions inhibiting expression of the growth-promoting gene.

4. An astrocyte that is transfected with an externally-regulated growth promoting gene and is produced according to the method of claim 3.

5. A neuron that is transfected with an externally-regulated growth promoting gene and is produced according to the method of claim 3.

6. A method for producing astrocytes and neurons, wherein the number of neurons produced predominates over the number of astrocytes produced, comprising culturing a conditionally-immortalized clonal human CNS progenitor cell that is transfected with an externally-regulated growth promoting gene in serum-free medium under conditions inhibiting expression of the growth promoting gene.

7. An astrocyte that is transfected with an externally-regulated growth promoting gene and is produced according to the method of claim 6.

8. A neuron that is transfected with an externally-regulated growth promoting gene and is produced according to the method of claim 6.

9. A method for screening for an agent that modulates activity of a protein produced by a CNS cell, comprising:
   (a) contacting a cell produced according to the method of claim 1 or claim 3 with a candidate agent; and
   (b) subsequently determining whether said candidate agent detectably suppresses or enhances an activity of a protein produced by said cell, wherein the protein is an ion channel, a growth factor receptor, a neurotransmitter receptor, a transcription factor, a MAP kinase, a caspase, a presinillin or an amyloid precursor protein; and therefrom determining whether the candidate agent modulates an activity of a protein produced by a CNS cell.

10. A method for screening for an agent that modulates activity of a protein produced by a CNS cell, comprising:
    (a) contacting a conditionally-immortalized clonal human CNS progenitor cell that is transfected with an externally-regulated growth promoting gene with a candidate agent; and
    (b) subsequently determining whether said candidate agent detectable suppresses or enhances an activity of a protein produced by said cell, wherein the protein is an ion channel, a growth factor receptor, a neurotransmitter receptor, a transcription factor, a MAP kinase, a caspase, a presinillin or an amyloid precursor protein; and therefrom determining whether the candidate agent modulates an activity of a protein produced by a CNS cell.

11. A method for detecting the presence or absence of a protein in a sample, comprising
    (a) contacting a sample with a cell produced according to the method of claim 1 or claim 3; and
    (b) subsequently detecting a response in said cell, wherein the response is indicative of the presence or absence of a protein in said cell, wherein the protein is an ion channel, a growth factor receptor, a neurotransmitter receptor, a transcription factor, a MAP kinase, a caspase, a presinillin or an amyloid precursor protein.

12. A method for detecting the presence or absence of a protein in a sample, comprising
    (a) contacting a sample with a conditionally-immortalized clonal human CNS progenitor cell that is transfected with an eternally-regulated growth promoting gene; and
    (b) subsequently detecting a response in said cell, wherein the response is indicative of the presence or absence of a protein in said sample, wherein the protein is an ion channel, a growth factor receptor, a neurotransmitter receptor, a transcription factor, a MAP kinase, a caspase, a presinillin or an amyloid precursor protein.

13. A method for screening for an agent that affects CNS cell death, comprising:
    (a) contacting a cell produced according to the method of claim 1 or claim 3 with a candidate agent under conditions that, in the absence of candidate agent, result in death of said cell; and
    (b) subsequently measuring the ability of said candidate agent to affect the death of said cell.

14. A method for screening for an agent that affects CNS cell death, comprising:
    (a) contacting a conditionally-immortalized clonal human CNS progenitor cell that is transfected with an externally-regulated growth promoting gene with a candidate agent under conditions that, in the absence of candidate agent, result in death of said cell; and (b) subsequently measuring the ability of said candidate agent to affect the death of said cell.

15. A method for screening for a protein that regulates CNS cell death, comprising:
   (a) altering the level of expression of a protein within a cell produced according to claim 1 or claim 3; and
   (b) subsequently measuring the affect of said alteration on the death of said cell, and thereby identifying a protein that regulates CNS cell death.

16. A method for screening for a protein that regulates CNS cell death, comprising:
   (a) altering the level of expression of a protein within a conditionally-immortalized clonal human CNS progenitor cell that is transfected with an externally-regulated growth promoting gene; and
   (b) subsequently measuring the affect of said alteration on the death of said cell, and thereby identifying a protein that regulates CNS cell death.

17. A conditionally-immortalized human CNS progenitor cell that is transfected with a gene encoding a growth-promoting protein, wherein said cell differentiates into neurons and astrocytes, but not into oligodendrocytes, and wherein said cell is produced according to the method of claim 1.

18. A cell according to claim 17, wherein said cell is present within a clonal cell line.

19. A cell according to claim 17, wherein said cell differentiates into neurons and astrocytes following suppression of production or activity of the growth-promoting protein.

20. A cell according to claim 17, wherein said cell differentiates into neurons following suppression of production or activity of the growth-promoting protein.

21. A cell according to claim 17, wherein said cell differentiates in the presence of serum predominantly into astrocytes following suppression of production or activity of the growth-promoting protein.

22. A method for producing neurons, comprising culturing a cell produced according to claim 1 under conditions inhibiting expression of the growth-promoting gene, wherein said culturing is performed in the presence of forskolin or the combination of NT-3, GDNF and BDNF, and in the absence of serum and PMA.

23. A method for producing astrocytes, comprising culturing a cell produced according to claim 1 under conditions inhibiting expression of the growth-promoting gene, wherein said culturing is performed in the presence of PMA, and in the absence of serum.

* * * * *

```
                        SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (xi) SEQUENCE DESCRIPTION: SEQ ID NO:1:

AACCTGCAGA ACCGCAAG                                                       18

(2) INFORMATION FOR SEQ ID NO:2:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (xi) SEQUENCE DESCRIPTION: SEQ ID NO:2:

GCTTGATGAG CAGGTCTATG C                                                   21

(2) INFORMATION FOR SEQ ID NO:3:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (xi) SEQUENCE DESCRIPTION: SEQ ID NO:3:

AGATTTGCTT TGTGGCAA                                                       18

(2) INFORMATION FOR SEQ ID NO:4:

(i) SEQUENCE CHARACTERISTICS:
         (A) LENGTH: 18 base pairs
         (B) TYPE: nucleic acid
         (C) STRANDEDNESS: single
         (D) TOPOLOGY: linear
```

(xi) SEQUENCE DESCRIPTION: SEQ ID NO:4:

ATTCTCCAGG TCCTGAAA                                             18

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:5:

CGGAAGATTG GCTACTGG                                             18

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:6:

TTAGCCGTGT AGGAGGAG                                             18

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:7:

GACACACGAC GCAATACTGG                                           20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

TGAGAATACG CCTGGTTTTG                                           20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:9:

TGGTACGAGA GGAGGTCATT                                           20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:10:

TCTGGCTTTG TTTCTTATGG                                          20

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:11:

CAAAGACAAG TCCAGCAA                                            18

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:12:

CCAACTCCAA ACCAGAAA                                            18

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:13:

TTTGCTGGAT GGATTTATG                                           19

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:14:

AAAGAACGAT TGGATAAGG                                           19

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:15:

GCGTCTTCTC CTTCCTCAAT C                                        21

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear -continued (xi) SEQUENCE DESCRIPTION: SEQ ID NO:16:

ATGCCCTCCT CGTTGTTCTT C                                                      21